US005766875A

United States Patent [19]
Hafeman et al.

[11] Patent Number: 5,766,875
[45] Date of Patent: Jun. 16, 1998

[54] METABOLIC MONITORING OF CELLS IN A MICROPLATE READER

[75] Inventors: Dean G. Hafeman, Hillsborough; Kimberly L. Crawford, Cupertino; Anthony J. Sanchez, San Bruno; Henry Garrett Wada, Atherton, all of Calif.

[73] Assignee: Molecular Devices Corporation, Sunnyvale, Calif.

[21] Appl. No.: 379,532

[22] PCT Filed: Jul. 30, 1993

[86] PCT No.: PCT/US93/07177

§ 371 Date: Jan. 31, 1995

§ 102(e) Date: Jan. 31, 1995

[87] PCT Pub. No.: WO91/03191

PCT Pub. Date: Feb. 17, 1994

[51] Int. Cl.[6] .............. C12Q 1/02; C12Q 1/00; C12N 5/00; G01N 33/00
[52] U.S. Cl. .............. 435/29; 435/4; 435/240.1; 435/240.2; 422/50; 422/55; 422/68.1; 436/34; 436/164; 436/805; 436/809; 356/4.01
[58] Field of Search ............. 435/29, 4, 287, 435/291, 240.1, 240.2; 436/34, 63, 164, 172, 805, 809; 422/68.1, 50, 55; 356/4.01

[56] References Cited

U.S. PATENT DOCUMENTS

| | | | |
|---|---|---|---|
| 4,448,534 | 5/1984 | Wertz et al. | 356/435 |
| 4,456,380 | 6/1984 | Kondo et al. | 356/418 |
| 4,568,186 | 2/1986 | Yoshimura et al. | 356/308 |
| 4,968,148 | 11/1990 | Chow et al. | 356/427 |
| 4,986,665 | 1/1991 | Yamanashi et al. | 356/402 |
| 5,112,134 | 5/1992 | Chow et al. | 356/427 |

FOREIGN PATENT DOCUMENTS

4016260 A1  12/1990  Germany.

OTHER PUBLICATIONS

Satoh et al. (1990). "Simultaneous Assay for Megakaryocyte Colony-Stimulating Factor and Megakaryocyte Potentiator and Its Application." *J. Lab. Clin. Med.*, vol. 116, pp. 162–171. Month not available.

Burstein et al. (1985). "Quantitation of Megakaryocytopoiesis in Liquid Culture by Enzymatic Determination of Acetylcholinesterase." *J. Cell. Physiol.*, vol. 122, pp. 159–165. Month not available.

(List continued on next page.)

*Primary Examiner*—Louise Leary
*Attorney, Agent, or Firm*—McDonnell Boehnen Hulbert & Berghoff

[57] ABSTRACT

The present invention method may be practiced with many different types of biological cells. Biological cells may be either eucaryotic or procaryotic cells. The cells may be in the form of tissue slices or tissue homogenates or may be in the form of suspensions of intact single cells. The intact single cells may be grown in cell culture, as described in the previous examples, or may be obtained from blood, other body fluids, or from tissue biopsy. The cells may be cells containing receptors transfected by recombinant DNA techniques, or alternatively may be cells naturally responding to cell-affecting agents. The cells may be fresh or may have been previously preserved by dehydration, refrigeration, or freezing. When the cells have been preserved, preservative agents (for example dimethylsulfoxide in the case of frozen cells) may be removed prior to measurement of the effect of cell-affecting agents on rates of extracellular acidification. The cells may be either plant cells or animal cells. The cells also may be obtained from fresh or salt water samples. The biological cells also may be microbial cells including bacteria, rickettsia, or mycoplasma. Also, various types of fungi, including yeast, may be employed. Other types of cells include algae, protozoans, and the like. The cells may also be unable to reproduce. That is, the cells may be made synthetically, for example by encapsulation of enzymes capable of causing a change in extracellular acidification upon providing a suitable enzyme substrate.

37 Claims, 12 Drawing Sheets

OTHER PUBLICATIONS

Wosu (1984), "In Vitro Studies on Feline Panleucopenia Virus. Standardization of Hemagglutination–Inhibition Test for Feline Panleucopenia Virus Antibody," *Comp. Immunol. Microbiol. Infect. Dis.*, vol. 7, pp. 201–206. Month not available.

Hernandez et. al. (1990), "FIA–Spectrophotometric Assay of N–Acetylcysteine by O–Phthalaldehyde Derivatization," *Pharmazie (Germany)*, vol. 45, pp. 745–747. Month not available.

Kulanthaivel et al. (1990), "The ATP–Binding Site of the Human Placental $H^+$ Pump contains Essential Tyrosyl Residues," *Biochemistry*, vol. 29, pp. 10807–10813. Month not available.

Sharp et al. (1990), "The Association of Platelet and Red Cell Count with Platelet Impedance Changes in Whole Blood and Light–Scattering Changes in Platelet Rich Plasma: Evidence from the Caerphilly Collaborative Heart Disease Study," *Thromb. Haemost.*, vol. 64, pp. 211–215. Month not available.

Malmer et al. (1990), "Amino Acid Analysis by High–Performance Liquid Chromatography with Methanesulfonic Acid Hydrolysis and 9–Fluorenylmethylchloroformate Derivatization," *J. Chromatogr.*, vol. 514, pp. 227–239. Month not available.

Thiel, (1990), "Determination of Moniliformin by High–Performance Liquid Chromatography," *J. Environ. Pathol. Toxicol. Oncol.*, vol. 10, pp. 162–165. Month not available.

Sethi et al. (1990), "Bb Fragment of Bovine Complement Factor B: Stimulation of the Oxidative Burst in Bovine Monocytes," *Can. J. Vet. Res.*, vol. 54, pp. 410–414. Month not available.

Pape et al. (1990), "Perturbation of Sacroplasmic Reticulum Calcium Release and Phenol Red Absorbance Transients by Large Concentrations of Fura–2 Injected into Frog Skeletal Muscle Fibers," *J. Gen. Physiol.*, vol. 96, pp. 493–516. Month not available.

Hollingworth et al. (1990), "Changes in Phenol Red Absorbance in Response to Electrical Stimulation of Frog Skeletal Muscle Fibers," *J. Gen. Physiol.*, vol. 96, pp. 473–491. Month not available.

Baylor et al. (1990), "Absorbance Signals from Resting Frog Skeletal Muscle Fibers Injected with the pH Indicator Dye, Phenol Red," *J. Gen. Physiol.*, vol. 96, pp. 449–471. Month not available.

Shiau et al. (1990), "Acidic Mucin Layer Facilitates Micelle Dissociation and Fatty Acid Diffusion," *Am. J. Physiol.*, vol. 259, pp. G671–G675. Month not available.

Letellier et al. (1991), "Determination of affinity of *Pasteurella multocida* Isolates for Porcine Respiratory Tract Mucus, and Partial Characterization of the Receptors," *Am. J. Vet. Res.*, vol. 52, pp. 34–39. Month not available.

Zebrev et al. (1990), "Zavisimoe to Mg2+ Tormozhenie Adgezii Leikotsitov, vyzvannoe Doksitsiklinom," *Antibiot. Khimioter*, vol. 35, pp. The English translation of the abstract of this article is provided. Month not available.

Fratantoni et al. (1990), "Measuring Platelet Aggregation with Microplate Reader. A New Technical Approach to Platelet Aggregation Studies," *Am. J. Clin. Pathol.*, vol. 94, pp. 613–617. Month not available.

Mayo et al. (1990), "Kinetic Microplate Assay for Superoxide Production by Neutrophils and Other Phagocytic Cells," *Meth. Enzymol.*, vol. 186, pp. 567–575. Month not available.

Bullock et al. (1990), "An Enzyme–Assessed Microplate–Assay for Neutrophil Adherence. I. IgA–Included Adherence of Human PMNs," *Inflammation*, vol. 14, pp. 427–445. Month not available.

Kobayashi et al. (1990), "Increased $Na^+$–$H^+$ Exchange Activity in Cultured Vascular Smooth Muscle Cells from Stroke–Prone Spontaneously Hypertensive Rats," *J. Hypertens.*, vol. 8, pp. 153–157. Month not available.

Tamm et al. (1990), "Insulin–Like Growth Factor–1 (IGF–1), Insulin, and Epidermal Growth Factor (EGF) are Survival Factors for Density–Inhibited, Quiescent Balb/c–3T3 Murine Fibroblasts," *J. Cell. Physiol.*, vol. 143), pp. 494–500. Month not available.

Taki et al. (1990), "A Simple and Specific Assay of Glycosyltransferase and Glycosidase Activities by an Enzyme–Linked Immunosorbent Assay Method, and Its Application to Assay of Galactosyltransferase Activity in Sera from Patients with Cancer," *J. Biochem.*, vol. 107, pp. 493–498. Month not available.

Yoshimura et al. (1990), "Novel Screening Method for Agents that Overcome Classical Multidrug Resistance in a Human Cell Line," *Cancer Lett.*, vol. 50, pp. 45–51. Month not available.

Kotyk et al. (1989), *Intracellular pH and Its Measurement*, pp. 69–85. Month not available.

O'Leary et al. (1983), "Optical Methods for Monitoring Temperature in Spectrophotometric Analysers," *Ann. Clin. Biochem.*, vol. 20, pp. 153–157. Month not available.

Bowie et al. (1976), "Development of an Aqueous Temperature–Indicating Technique and Its Application to Clinical Laboratory Instrumentation," *Clin. Chem.*, vol. 22, pp. 449–455. Month not available.

Schilling et al. (1992), "Überprüfung der Temperierung von Mikrotiterplatten in thermostatisierbaren Readern mit einem hochauflösenden optischen Thermometer," *BL–Journal*, vol. 2, pp. 77–80. Month not available.

Parce et al. (1989), "Detection of Cell Affecting Agents with a Silicon Biosensor," *Science*, vol. 246,pp. 243–247. Month not available.

Owicki et al. (1990), "Bioassays with a Microphysiometer," *Nature*, vol. 344, pp. 271–272. Month not available.

Owicki et al. (1990), "Continuous Monitoring of Receptor–Mediated Changes in the Metabolic Rates of Living Cells," *Proc Natl. Acad. Sci U.S.A.*, vol. 87, pp. 4007–4011. Month not available.

Parce et al. (1990), "The Silicon Microphysiometer: Detection of Biological Effects of Chemical and Biochemical Agents by Alterations of Cellular Metabolic Rate,", *Biosensor Technology, Fundamentals and Applications*, pp. 367–373. Month not available.

Parce et al. (1990), "Biosensors for Directly Measuring Cell–Affecting Agents," *Ann. Biol. Clin.*, vol. 48, pp. 639–641. Month not available.

Wada et al. (1991), "Cells on Silicon: Bioassays with a Microphysiometer," *Clin. Chem.*, vol. 37, pp. 600–601. Month not available.

Bruner et al. (1991), "Testing Ocular Irritancy In Vitro with the Silicon Microphysiometer," *Toxic. in Vitro*, vol. 5, pp. 277–284. Month not available.

Parce et al. (1991), "Cells on Silicon: The Microphysiometer," *In Vitro Toxicology: Mechanisms and New Technology*, vol. 8, pp. 97–106. Month not available.

McConnell et al. (1991), "The Microphysiometer Biosensor," *Current Opinion in Structural Biology*, vol. 1, pp. 647–652. Month not available.

Raley–Susman et al. (1992). "Effects of Exitotoxin Exposure on Metabolic Rate of Primary Hippocampal Cultures: Application of Silicon Microphysiometry to Neurobiology." *J. Neuroscience*, vol. 12, pp. 773–780. Month not available.

Owicki et al. (1992). "Biosensors Based on the Energy Metabolism of Living Cells: the Physical Chemistry and Cell Biology of Extracellular Acidification." *Biosensors and Bioelectronics*, vol. 7, pp. 255–272. Month not available.

Nag et al. (1992). "Antigen–Specific Stimulation of T Cell Extracellular Acidification by MHC class II–Peptide Complexes." *Immunol*, vol. 148, pp. 2040–2044. Month not available.

McConnell et al. (1992). "The Cytosensor Microphysiometer: Biological Applications of Silicon Technology." *Science*, vol. 257, pp. 1906–1912. Month not available.

Wada et al. (1993). "GM–CSF Triggers a Rapid Glucose Dependent Extracellular Acidification by TF–1 Cells. Evidence for Sodium/Proton Antiporter and PKC Mediated Activation of Acid Production." *J. Cell. Physiol.*, vol. 154, pp. 129–138. Month not available.

Wada et al. (1992). "Measurement of Cellular Responses to Toxic Agents Using a Silicon Microphysiometer." *Alternatives to Animal Testing and Experiments*, vol. 1, pp. 154–164. Month not available.

Baxter et al. (1992). "PKCε Is Involved in GM–CSF Signal Transduction. Evidence from Microphysiometry and Antisense Oligonucleotide Experments." *Biochemistry*, vol. 31, pp. 10950–10954. Month not available.

Miller et al. (1993). "Cholinergic Stimulation of the Na+/K+ ATPase as Revealed by Microphysiometry." *Biophys.*, vol. 64, pp. 813–823. Month not available.

Nag et al. (1993). "Purified β–Chain of MHC Class II Binds to CD4 Molecules on Transfected HeLa Cells." *J. Immunol.*, vol. 150, pp. 1358–1364. Month not available.

Nag et al. (1993). "Stimulation of T Cells by Antigenic Peptide Complexed with Isolated Chains of Major Histocompatibility Complex Class II Molecules." *Proc. Natl. Acad. Sci. USA*, vol. 90, pp. 1604–1608. Month not available.

Dawson, et al. (1986). "The Antiproliferative Activity of Interferons Assayed by Measuring Growth Medium Color Changes Related to Cell Number." *J Interferon Res.*, vol. 6, pp. 137–142. Month not available.

Kuchler, et al. (1977). "Milieu For Maintaining and Growing Animal Cell In Vitro." *Bioch Meth. Cell Cult. Virol.*, pp. 56–58. Month not available.

Fisher Scientific Catalog (Biotechnology Source (1987), p. 128. Month not available.

THERMOmax Microplate Reader User's Manual, Molecular Devices Corp., Copyright 1989, U.S.A. Month not available.

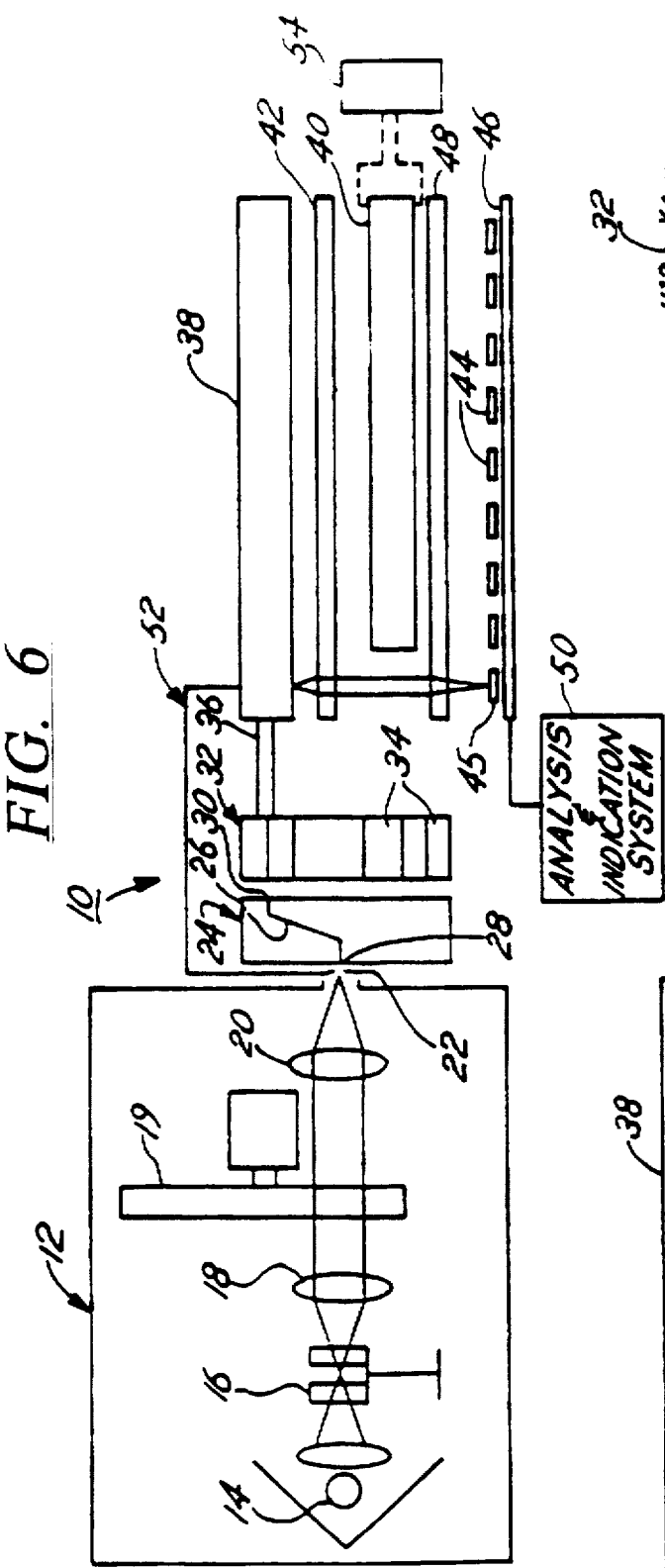
FIG. 6
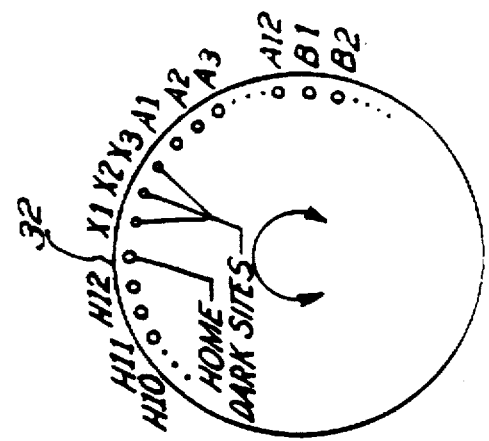
FIG. 8
FIG. 7

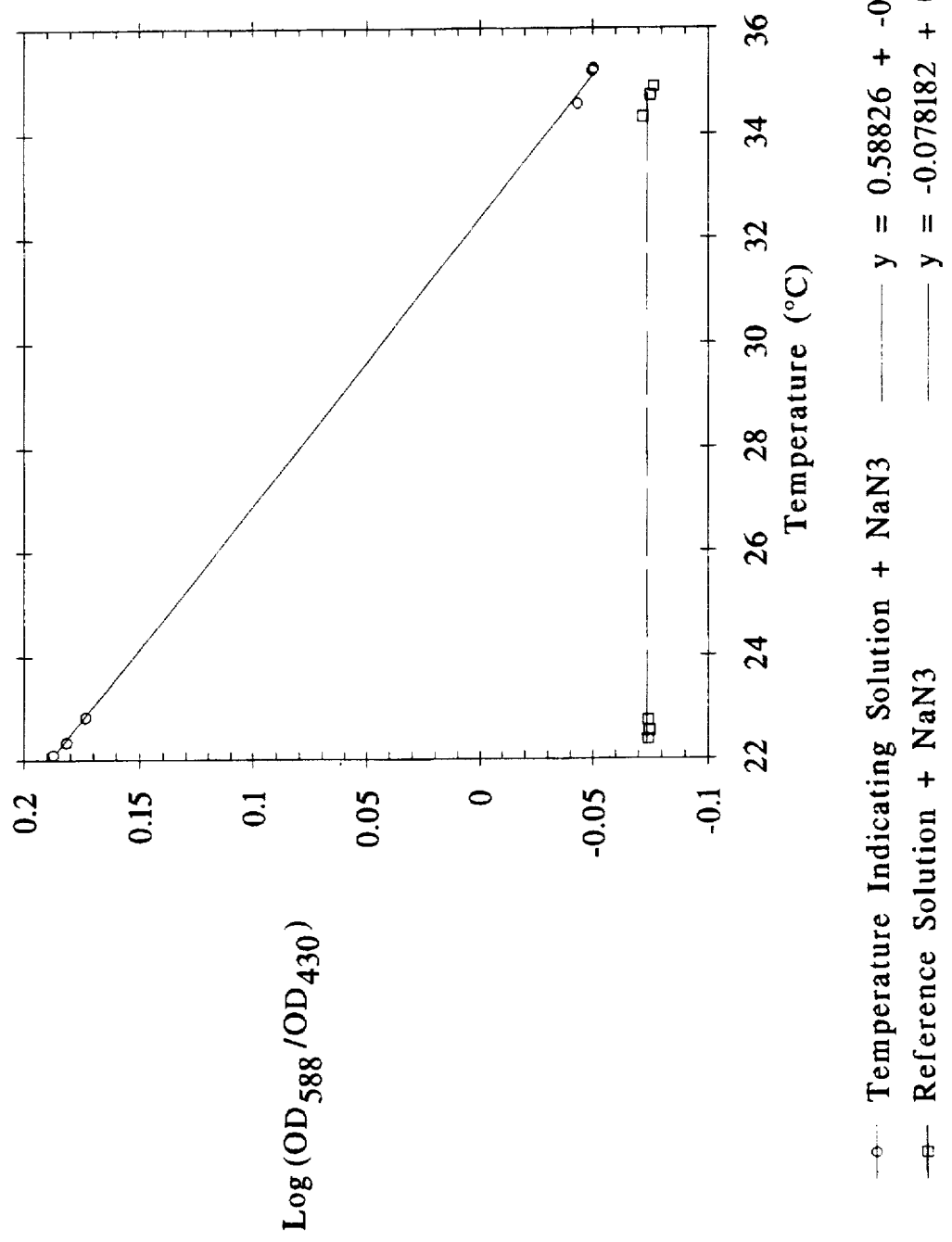

$\text{Log}\dfrac{(OD_{560}-OD_{650})}{(OD_{420}-OD_{650})}$ - Y-Intercept at 26°C

- HEPES     y = 0.10188 + -0.0039184x   R=0.99949
- PBS     y = -0.13924 + 0.0053552x   R= 0.99874
- PBS+1.0 M NaCl     y = -0.17399 + 0.0066921x   R= 0.9984
- Phosphate Buffer pH=7.0     y = -0.12266 + 0.0047178x   R= 0.99994
- TRIS     y = 0.38816 + -0.014929x   R= 0.99962
- TRIS+1.0 M NaCl     y = 0.34728 + -0.013357x   R= 0.99933
- Citrate     y = -0.20956 + 0.0080601x   R= 0.99994
- Citrate+1.0 M NaCl     y = -0.19502 + 0.007501x   R= 0.99994
- MES     y = 0.12321 + -0.0047388x   R= 0.99943
- MOPS     y = 0.018325 + -0.00070368x   R= 0.8877
- EDTA     y = 0.020099 + -0.00077286x   R= 0.99586
- TAPS     y = 0.31394 + -0.012076x   R= 0.99948

1

METABOLIC MONITORING OF CELLS IN A MICROPLATE READER

FIELD OF INVENTION

This invention generally relates to a method for monitoring the metabolism of cells. e.g. metabolic extracellular acid production. More particularly, this invention comprises the steps of placing the cells in a buffer containing an acid/base indicator and placing the cell/buffer solution in wells of a multiassay plate. heating the solution to about 37 degrees centigrade, mixing the solution in the multiassay plate, measuring the ratio of the optical density of the acid/base indicator at more than one different wavelength of light passing vertically through the solution, and repeating the mixing and measuring steps to kinetically monitor the rate of change in extracellular pH with extremely high precision.

BACKGROUND OF THE INVENTION

A variety of techniques and devices are commercially available for the detection and measurement of substances present in fluid or other translucent samples by determining the light transmittance of the sample. Similarly, absorptive and fluorescent acid/base indicator dyes have been used to indicate the pH of aqueous sample compartments as small as individual living cells (Arnost Kotyk and Jan Slavik. Assays of Intracellular pH Using Chemical Probes: Absorption Spectroscopy, *Intracellular pH and Its Measurement*, pp. 69–85. CRC Press, Bocca Raton, Fla., 1989.) However, the pH of samples can change with a change in temperature, and can cause inaccuracies in measurement. An example of how the pH of pure water is different at temperatures of 25° C. and 37° C. is shown as follows.

It is well known that the pH of pure water at 25° C. is 7.0. The necessary equation to calculate the pH of pure water at 37° C. is:

$$ln(K_2/K_1) = -(\Delta H°/R)((1/T_2)-(1/T_1))$$

The ionization constant of water is $10^{-14}$ at 25° C., its $\Delta H° = 13.5$ kcal, $K_1 = 10^{-14}$, $\Delta H° = 13.5$ kcal, $T_1 = 298$, and $T_2 = 310$. Then $$\ln(K_2/10^{-14}) = -(13,500/1.99)((1/310)-(1/298))$$
$$= +0.88$$
$$K_2/10^{-14} = e^{+0.88} = 2.4$$
$$K_2 = 2.4 \times 10^{-14}$$

This is the ionization constant of water at 37° C. The $H^+$ and $OH^-$ in pure water is surely low enough so that the activities of the ions equal concentrations: $[H^+]=[OH^-]$. At 37° C., $[H^+][OH^-]=2.4\times10^{-14}$ $[H^+]=1.55\times10^{-7}$ $pH=-\log[H^+]=6.81$ Similarly, the $pK_a$ values of both buffering systems and acid-base indicators change with temperature. For example, the change in absorbance of Cresol Red, at 575 nanometers, in a TRIS (tris[Hydroxymethyl]aminomethane) buffer system, has been used to monitor temperature changes (K. Schilling, H. Hoppe and A. Horn, Überprüfung der Termperierung von Mikrotiterplatten in Thermaostatisierbaren Readern mit einem hochauflösenden optischen Thermometer, *BL Journal* (3) 77–80, 1992; T. D. O'Leary, J. L. Badennoch and R. Bais, Optical Methods for Monitoring Temperature in Spectrophotometric Analysers, *Ann. Clin. Biochem*. 20, 153–157, 1983; L. Bowie, F. Esters, J. Bolin and N. Gochman, Development of an Aqueous Temperature-Indicating Technique and Its Application to Clinical Laboratory Instrumentation, *Clin. Chem*. 22/4, 449–455, 1976).

The present invention incorporates by reference the "Background of the Invention" for U.S. Pat. Nos. 4,968,148 and 5,112,134. As discussed in U.S. Pat. Nos. 4,968,148 and 5,112,134, the prior art has many problems and limitations. Although the vertical beam absorbance reader, taught in U.S. Pat. Nos. 4,968,148 and 5,112,134, solves or diminishes these problems and limitations, it has been discovered that buffer and pH indicator dye temperature effects and temperature fluctuation and light scatter interferences in the pH monitoring of cells in microplates can obscure the measurement of metabolic extracellular acid production.

SUMMARY AND OBJECTS OF THE INVENTION

It is the primary objective of this invention to provide an improved method of using the inventions of U.S. Pat. No. 4,968,148 and 5,112,134. More particularly, the present invention comprises steps that balance both buffer and pH indicator dye temperature effects. The present invention also compensates for temperature fluctuation, light scatter interferences, and light absorbance path length fluctuation in pH monitoring of cells in microplates. These inventive steps result in a more accurate measurement of metabolic extracellular acid production and also provide an improved method for measuring temperature of solutions spectrophotometrically.

The present invention uses a combination of an assay medium formulation to balance both buffer and pH indicator dye temperature effects, and a measurement of the ratio of absorbance at different wavelengths, e.g., 560 nm and 420 nm optical density ("OD") for phenol red acid/base indicator to compensate for temperature fluctuation and light scatter interferences in pH monitoring of cells in microplates. Those skilled in this art will recognize a wide variety of acid/base indicators and respective absorption maxima for the acid form and the base form of such indicators. Other examples of acid/base indicators include bromothymol blue (3',3"-Dibromothymolsulfonephthalein; molecular formula: $C_{27}H_{27}Br_2NaO_5S$), bromocresol purple and the like. Those skilled in this art will recognize a wide variety of such indicators. The method of the present invention also includes the repeating of the mixing and measuring steps to reduce error in the measurement of extracellular acid production due to non-homogenous mixing of the sample.

BRIEF DESCRIPTION OF THE DRAWINGS

FIG. 6, 7, and 8 are illustrations, described in and the same as FIGS. 1–3 in U.S. Pat. No. 4,968,148.

FIG. 9 is a graph, further described in Example 1, that plots the log of measurements taken at 588 and 430 nm versus Temperature (°C.).

DESCRIPTION OF THE PREFERRED EMBODIMENT

While the invention will be described in connection with certain preferred embodiments, it will be understood that the description does not limit the invention to these particular embodiments. In fact, it is to be understood that all alternatives, modifications and equivalents are included and ar protected, consistent with the spirit and scope of the inventions as definer the appended claims.

Figure 1:
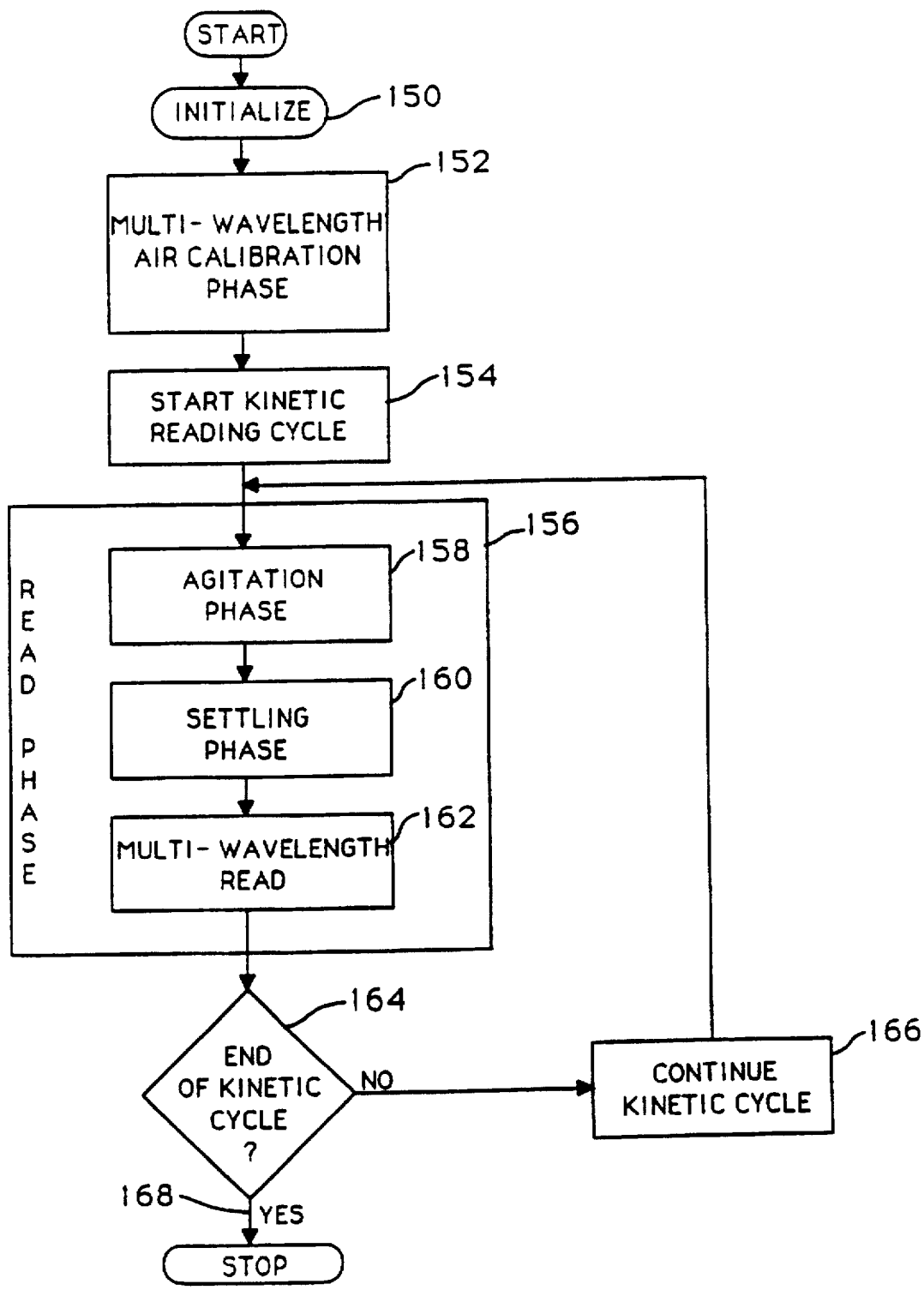
FIGS. 1 through 4 are flow diagrams, further described below.

According to this invention and improving upon U.S. Pat. No. 4,968,148, FIG. 1 is a flow diagram of the general sequence of operations involved in a typical sequential scan performed by a multi-well, vertical-beam photometer according to the system of this invention. The sequence begins at step 150 where the various system variables, such as the number of readings to be made within the kinetic reading cycle and the time at which they are made, duration of agitation, the duration of the delay following the agitation phase, etc., are initialized. At step 152, the air calibration phase is carried out by performing a measurement of light intensity through air of each optical path prior to introduction of samples. These values are stored in memory for subsequent reference. For multi-wavelength measurements, an air calibration is done for each wavelength and all values are stored in memory. Measurements made during the air calibration phase are performed with a unity gain setting G2 for a second variable gain amplifier 130 and the gain G1 of a first variable gain amplifier 120 is optimized for the maximum dynamic range of the analog-to-digital converter. (See, FIG. 5, which is the same as U.S. Pat. No. 4,968,148 FIG. 4, which shows a second variable gain amplifier 130 and a first variable gain amplifier 120). This various steps and measurements undergone as part of the air calibration phase 152 will be described in detail below.

The air calibration phase 152 is followed by step 154 where a kinetic reading cycle is initiated upon the basis of the initialization data provided to the measurement system as part of step 150. The kinetic reading cycle 154 includes the execution of the agitating, delay and multi-wavelength reading steps at each series of pre-programmed discrete time intervals at which optical readings are to be taken for the particular samples being measured. It will be apparent that, in the case of end-point analysis, the reading cycle will comprise the execution of the above steps only at a single time interval. In one embodiment of this invention, the number of data points read is held to a reasonable number even when the length of the assay is long. In this embodiment, at the start of an assay, data points are taken in relatively rapid succession (typically approximately 10 seconds, or 13 seconds when 3 seconds of agitation is utilized, between subsequent multi-wavelength reads of a single sample well), while later in the assay time between subsequent reads of a single sample well is increased. In this manner, when performing assays on chemistries which are rapidly changing in optical density, a large number of data points per sample are taken in a short period of time, while for chemistries which are slowly changing optical density, a number of data points per sample are taken over a longer period of time. In one embodiment, the time between subsequent readings of a single sample increases logarithmically with time. This effectively increases the dynamic range of rates of reaction, with greater accuracy.

Step 156 is the read phase, which includes a series of three steps beginning with the agitation phase 158 during which the sample plate is vibrated for a pre-defined time interval. Subsequently, at step 160, the settling phase takes place during a pre-defined delay interval in which the oscillation mechanism is dormant and the reaction agents within all the sample wells of the sample are allowed to settle down for a pre-defined time interval before obtaining the actual signal readings. At step 162, the measurement system obtains the transmittance readings (one for each wavelength) of all the wells of the sample plate. This step includes optimization, for each wavelength, of the gain setting G2 for the second variable gain amplifier 130 while maintaining the gain settings of G1 (for each wavelength) of the first variable gain amplifier 120 at the optimized value determined during air reference for each wavelength.

The sequence of events involved in the read step 162 will be described in detail below.

Following the read step 162, a check is made at step 164 to determine whether the system has completed the pre-defined kinetic reading cycle. If the answer at step 164 is no, step 166 continues the kinetic reading cycle. The read phase 156 is reiterated by the measurement system until the agitation phase and the accompanying delay and dual-wavelength read sequences have been performed at each of the prescribed time intervals, and when this occurs the measurement system comes to a stop. This marks the end of the kinetic reading cycle.

The reading cycle has been described above only with respect to the sequence of operations undergone by the illustrative photometric measurement device in obtaining the various light readings required to calculate the optical density at the sample sites for each wavelength. After each reading cycle is completed, the ratio of the wavelengths is calculated for each sample site. It will be understood that the microprocessor system, which forms part of the analysis and indication system shown in FIG. 1, processes the data resulting from the measurements as the reading cycle proceeds and initiates computation of optical density values (on the basis of a pre-defined algorithm as will be explained below) for those sample sites and time intervals for which required measurements have been completed. After the optical density values are obtained, the computation of the wavelength ratios is initiated (on the basis of a pre-defined algorithm as will be explained below) for each of the sample sites.

The following definitions and symbols will be used in the ensuing description of the various operations carried out by the measurement system of this invention during the air calibration and read phases.

$OD_{in}$: The calculated optical density for a particular wavelength (where i varies from 1 through 2 for the current embodiment, but preferably is not limited to two wavelengths) of a given sample well (where n varies from 1 through 96 in order to designate the 12 sample wells positioned along each of the 8 rows A through H of the microplate).

$W_a$: The signal output of a photodetector corresponding to a given sample well containing the reacting sample, where n varies from 1 through 96 in order to designate the position of sample wells, as above.

G1: The adjustable gain of the first stage variable gain amplifier 120 (controllable by a set a gain multiplication factors including 1, 2, 4, 8, 16, 32, 64 and 128).

G2: The adjustable gain factor for the second stage variable gain amplifier 130 (adjustable by a set of gain multiplication factors including 1, 10 and 100).

$D_a$: The dark current reading taken with the two-way switch 122 of FIG. 5 in its open position, for a given sample well. This reading is taken with the first stage gain setting G1 set to 1 and at the same second stage gain setting G2 used to obtain the corresponding Wn signal output.

W.AIR$_a$: The signal reading of a given sample well's air calibration taken with the secondary stage variable gain amplifier at a gain setting G2=1.

$D_{air}$: The dark current reading of an air calibration performed with the secondary stage gain setting G2=1.

L.REF$_{air}$: The light reference signal reading taken during an air calibration with the secondary stage gain setting G2=1.

L.REF$_{read}$: The light reference signal taken at the initiation of a READ cycle with the secondary stage variable gain setting G2=1.

$D_{read}$: The dark current readings taken at the beginning of a READ cycle.

Figure 2:
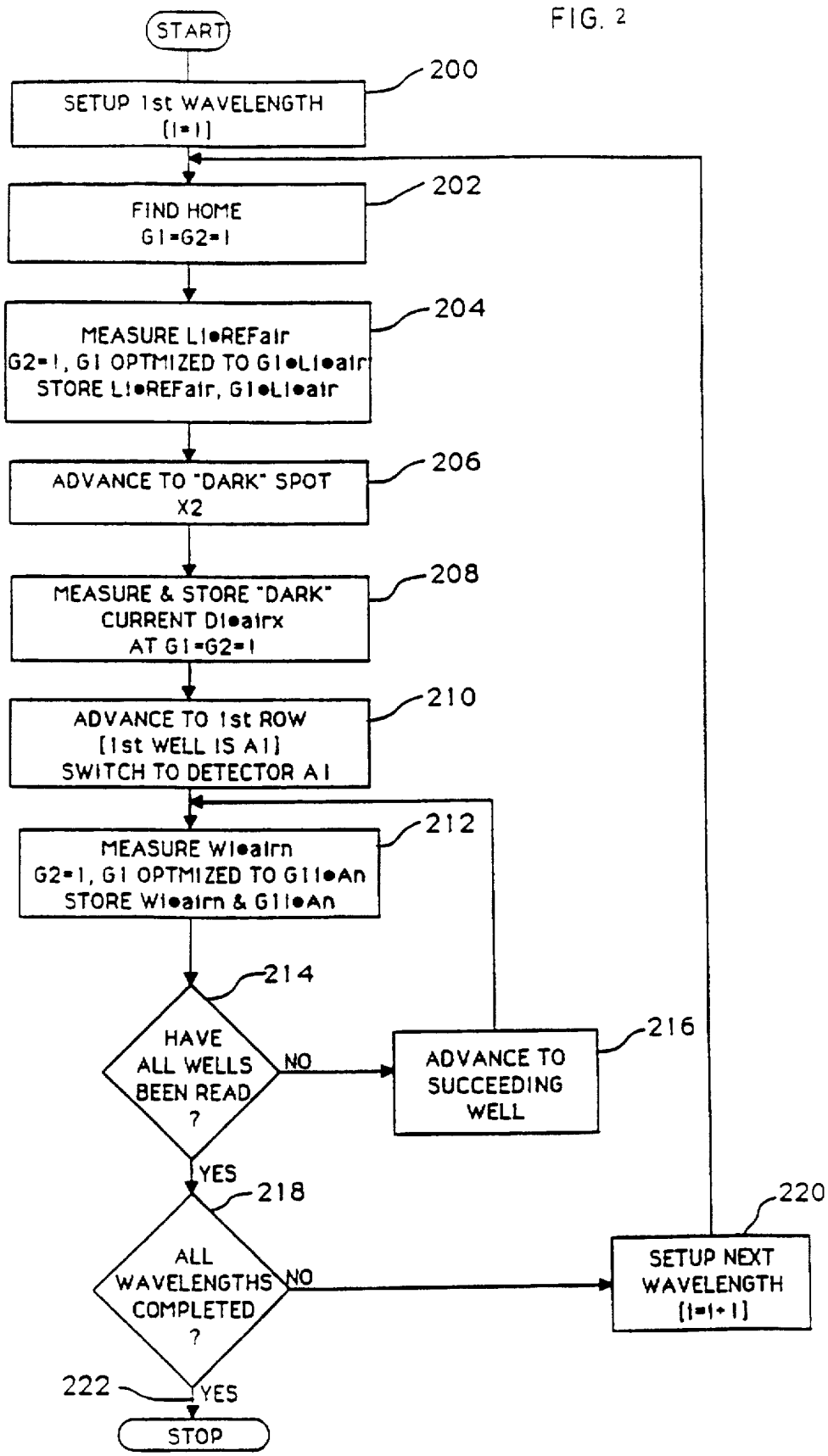

Referring now to FIG. 2, there is shown a flow chart of the sequence of operations included within the multi-wavelength air calibration phase of FIG. 1. At the first step 200, the measurement system selects the interference filter for the first wavelength of light to be used for air calibration.

At the next step 202, and with reference to FIG. 6, the measurement system positions the rotor 24 at the reference "home" position by sequentially displacing the rotor until the existence of a peak signal is detected at the output of the "home" reference photodetector. At this stage, the gain settings for both the first and second stage variable gain amplifiers 120 and 130 are set to unity. In an alternative embodiment, during the setting of the gain of amplifiers 120 and 130, the rotor is not located at a position corresponding to one of the three opaque spots on fiber distributor 32 since switch 122 is grounded.

The next step in the air calibration sequence is step 204 where the measurement system switches to either the photodetector for the light reference fiber or the photodetector for the home reference fiber in order to measure the light reference signal L.REF$_{air}$. This reading is measured with the gain G2 of the secondary stage variable gain amplifier set to unity and the gain G1 of the first stage variable gain amplifier optimized to provide the largest permitted count value at the output of the analog-to-digital converter 134 (according to the safety-adjusted dynamic ranging procedure described in U.S. Pat. Nos. 4,968,148 and 5,112,134). Also at step 204, the measured reference signal value L.REF$_{air}$ and the optimized first stage gain setting G1$_{L,air}$ are stored in the memory of the microprocessor system for later use in the optical density calculations.

At the succeeding step 206, the rotor is displaced through a designated number of positions relative to the "home" position so as to locate the rotor at a position corresponding to one of the three opaque spots $X_1$, $X_2$ and $X_3$ on the fiber distributor 32. According to the preferred embodiment, the rotor is actually displaced by three positions relative to its home position so that the coupler comes to rest at a position corresponding to the opaque spot $X_3$. In this position, the opaque spot effectively blocks the coupling of any light from the coupling fiber 26 into any of the fibers within the fiber manifold 32 and hence isolates the light source from the photodetectors.

At the succeeding step 208, the dual position dark current switch 122 is activated and a dark current reading $D_{air}$ is taken with both the first and second stage gain G1 and G2 set to unity. The dark current reading $D_{air}$ represents the residual current flowing within the portion of the processing circuitry of FIG. 1 following the two-way switch 122. This value is subtracted from the signal reading of every sample well in order to provide a true representation of the transmittance value for the sample well at any designated time. Also at step 208, the measured dark current reading $D_{air}$ is stored in the system memory for later use in calculating the optical density.

At this stage, the measurement system is ready to perform air calibration readings on each of the sample wells. Accordingly, at step 210, the rotor 24 is advanced to the position $A_1$ corresponding to the first sample well of the multiple well plate, and the photodetector corresponding to the sample well $A_1$ is switched on. At the succeeding step 212, the air calibration signal reading W.AIR$_a$ for sample well $A_1$ is taken with the gain G2 of the secondary stage variable gain amplifier set to unity and the gain G1 of the first stage variable gain amplifier optimized to a value G1$_{A1}$; the later value represents the gain setting which allows the maximum safety-adjusted output from the analog-to-digital converter without exceeding its rated dynamic range. At the end of step 212, the measured signal reading W.AIR$_a$ (in this case n=A$_1$) and the optimized gain setting G1$_{A1}$ are stored in the memory.

At step 214, the microprocessor system checks to determine whether air calibration has been performed at each of the 96 sample well sites on the sample microplate. If the answer at step 214 is negative, then step 216 advances the rotor to a position corresponding to the succeeding sample well site before reverting to the air calibration step 212. If the answer at step 214 is positive, i.e., air calibration has indeed been performed on all 96 sample well sites, it marks the end of the air calibration sequence for the current wavelength selected. At the next step 218, the microprocessor system checks to determine whether the air calibration has been completed for all of the wavelengths selected. If the answer at step 218 is negative, then step 220 advances the filter wheel to the next interference filter wheel specified before returning to the air calibration step 202 to find the "home" position. If the answer at step 218 is positive, then the air calibration phase has been performed for every wavelength specified.

It will be noted that the entire air calibration sequence is performed with the sample plate in its retracted position, i.e., away from the photodetector board so that light from the fiber manifold 38 is transmitted directly to the photodetectors and not through the samples.

Figure 3:
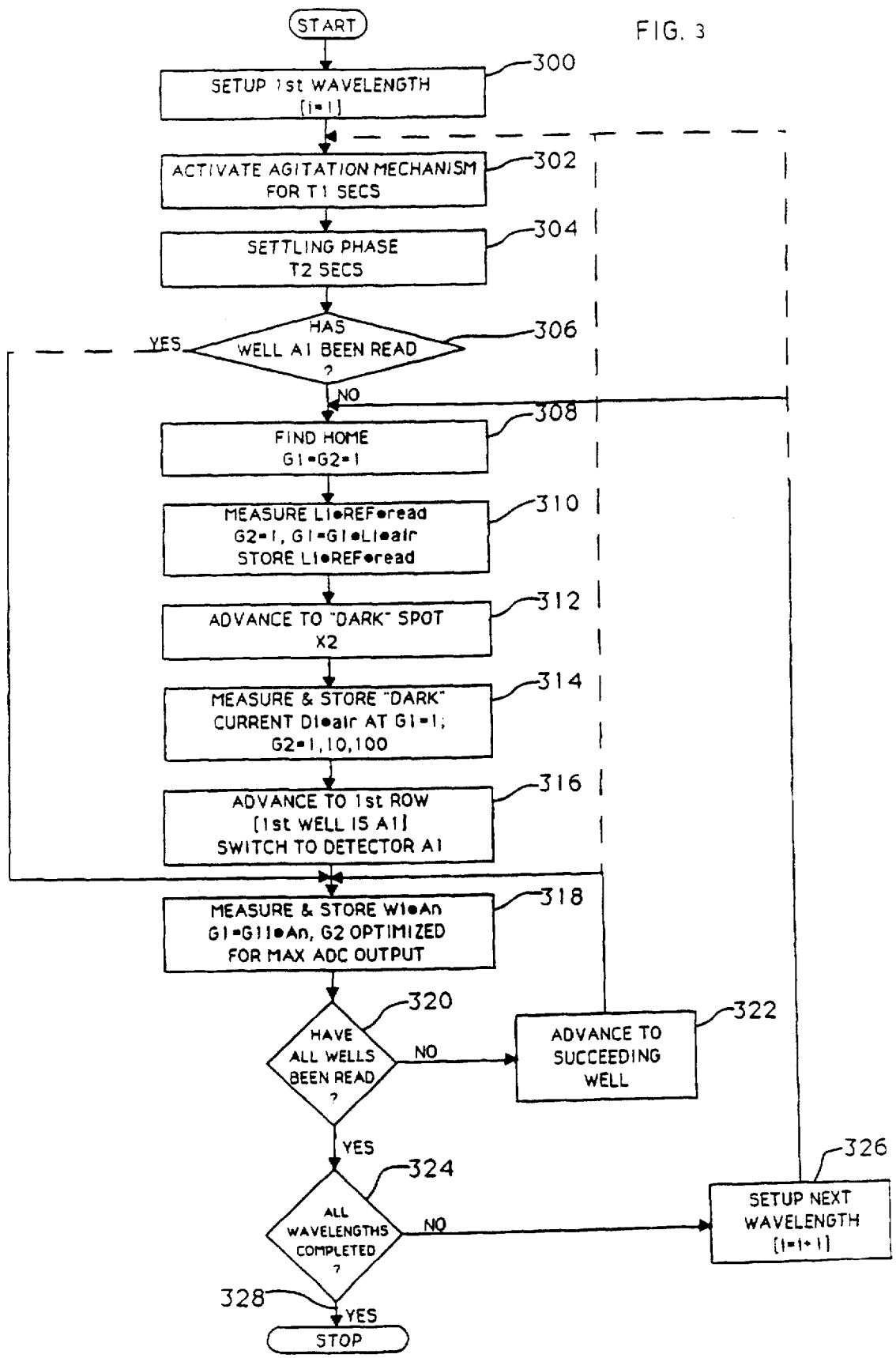

Referring now to FIG. 3, there is shown a flow chart of the sequence of operations undergone by the measurement system while performing the read phase during an end-point assay, i.e. an assay where, for example, samples are prepared in a multiple well microplate and a predetermined time passed to allow the chemistries to develop, at which time (the "end-point") an assay of the samples is performed. It should be noted that before actual reading is performed on a sample plate, the measurement system proceeds through the air calibration phase with the sample plate in its retracted position, i.e. not in the light path. Prior to the start of the read phase, the sample plate is moved into its advanced position, i.e. each sample is in a measured light path, in preparation for the reading phase.

At the start of a reading operation (step 300 in FIG. 3, the measurement system selects the interference filter for the first wavelength of light to be used for reading of the sample wells. In the next step 302, the measurement system activates the agitation mechanism for a predesignated time interval $T_1$ to promote homogeneous color distribution. The agitation phase of step 302 is succeeded by a settling phase at step 304, during which the agitation mechanism is deactivated and the system dwells for a time interval $T_2$ to allow the agitated samples to settle down in preparation for performing transmittance readings upon them. The agitation phase optimally comprises 0.042 inch amplitude oscillatory movement of a 96-well multiassay plate for 200 milliseconds at a frequency of 20 Hz followed by 200 milliseconds at 30 Hz. This cycle is repeated during a $T_1$ interval of 5 seconds. The interval $T_2$ is about 1 second.

The agitation phase at step 302 may entail displacement of the sample from its position between the fiber manifold and the photodetector board to permit oscillatory movement of the plate. Accordingly, the settling phase may actually take place during the time it takes to reposition the plate from its agitation position to its reading position. Immediately after agitation and the subsequent settling of the reacting samples within the sample plate, optical density readings are taken.

At step 306, the microprocessor system checks to see if the sample well located at position A1 has been read for this current wavelength. If the answer is positive, the system then proceeds to step 318 and performs the read for the current well position. If the answer at step 306 is negative, then the system proceeds to step 308.

At step 308, the measurement system locates the rotor at the "home" position. For this purpose, the signal from the "home" reference fiber photodetector is tracked by the processing circuitry with both the first and second stage variable gain amplifiers having their gains G1 and G2 set to unity.

Step 310 is then accessed, where a measurement of a light reference signal occurs. More specifically, the measurement system switches to the photodetector corresponding to the light reference fiber (or the photodetector corresponding to the home reference fiber if this fiber is being used to perform the functions of the light reference fiber), and a light reference signal L.REF$_{read}$ is taken with G2 set to unity and G1 optimized to its maximum value G1$_{L,air}$ according to the dynamic ranging procedure described above. Also as part of step 310, the measured L.REF$_{read}$ value is stored in the system memory for later use during calculations of optical density.

At the succeeding step 312, the rotor 24 is displaced through a designated number of positions to locate it at one of the three opaque spots $X_1$, $X_2$, $X_3$ provided on the fiber distributor 32. More specifically, the rotor is stepped three positions relative to the home reference fiber so as to be located at the third opaque spot $X_3$.

The following step 314 actuates the dual position switch 122 and measures a series of dark current readings D$_{air,x}$ with the first stage variable gain G1 set to unity. A single reading is taken at each of the possible gain settings G2 (in this case 1, 10 and 100) of the secondary stage variable gain amplifier. The measured values of D$_{air,x}$ are also stored within the system memory as part of step 314.

At the succeeding step 316, the rotor is advanced to the first sample well position $A_1$. In addition, the system switches to the photodetector corresponding to the first sample well $A_1$ to begin the actual sequential reading cycle.

At step 318, the signal W$_{An}$ for the first sample well, i.e., $A_1$ is measured with G1 set to the corresponding stored gain value GA$_1$, determined as part of the air calibration (step 212 in FIG. 2). During this measurement, G2 is initially set to unity and then optimized to a value that produces the maximum safety-adjusted out-put value from the analog-to-digital converter of FIG. 7 (see also. FIG. 2 of U.S. Pat. No. 4,968,148). Also, as part of step 318, the measured signal value WA$_1$ is stored within the system memory for use in calculation of the optical density for that sample well.

At the succeeding step 320, the microprocessor system performs a check to determine whether signal readings have been obtained for all 96 sample wells. If the answer at step 320 is negative, then the microprocessor system advances the rotor to a position corresponding to the next sample well. At the same time, the processing circuitry switches to monitor the photodetector corresponding to the selected sample well.

After the following step 322 in which the rotor and photodetector circuitry have advanced to the next well to be read, read step 318 is performed without repeating agitation step 302 and settling step 304. In this embodiment, a single agitation step 302 and settling step 304 are performed once prior to reading all 96 wells on the microplate. A positive answer at step 322 indicates that signal readings have been obtained from all sample wells.

This marks the end of the read operation sequence for the current wavelength selected. At the next step 324, the microprocessor system checks to determine whether the read phase has been completed for all the wavelengths selected. If the answer at step 324 is negative, then step 326 advances the filter wheel to the next interference filter specified before returning to the read step 308 to find the "home" position. If the answer at step 324 is positive, then the read phase has been performed for every wavelength specified.

In an alternative embodiment, shown by the dashed lines in FIG. 3, following steps 322 and 326, in which either the rotor or photodetector circuitry has advanced to the next well to be read or the next wavelength is selected before reading the plate again, the agitation and settling steps are repeated before reading. These steps are reiterated until the check at steps 320 or 324 produces a positive answer.

Figure 4:
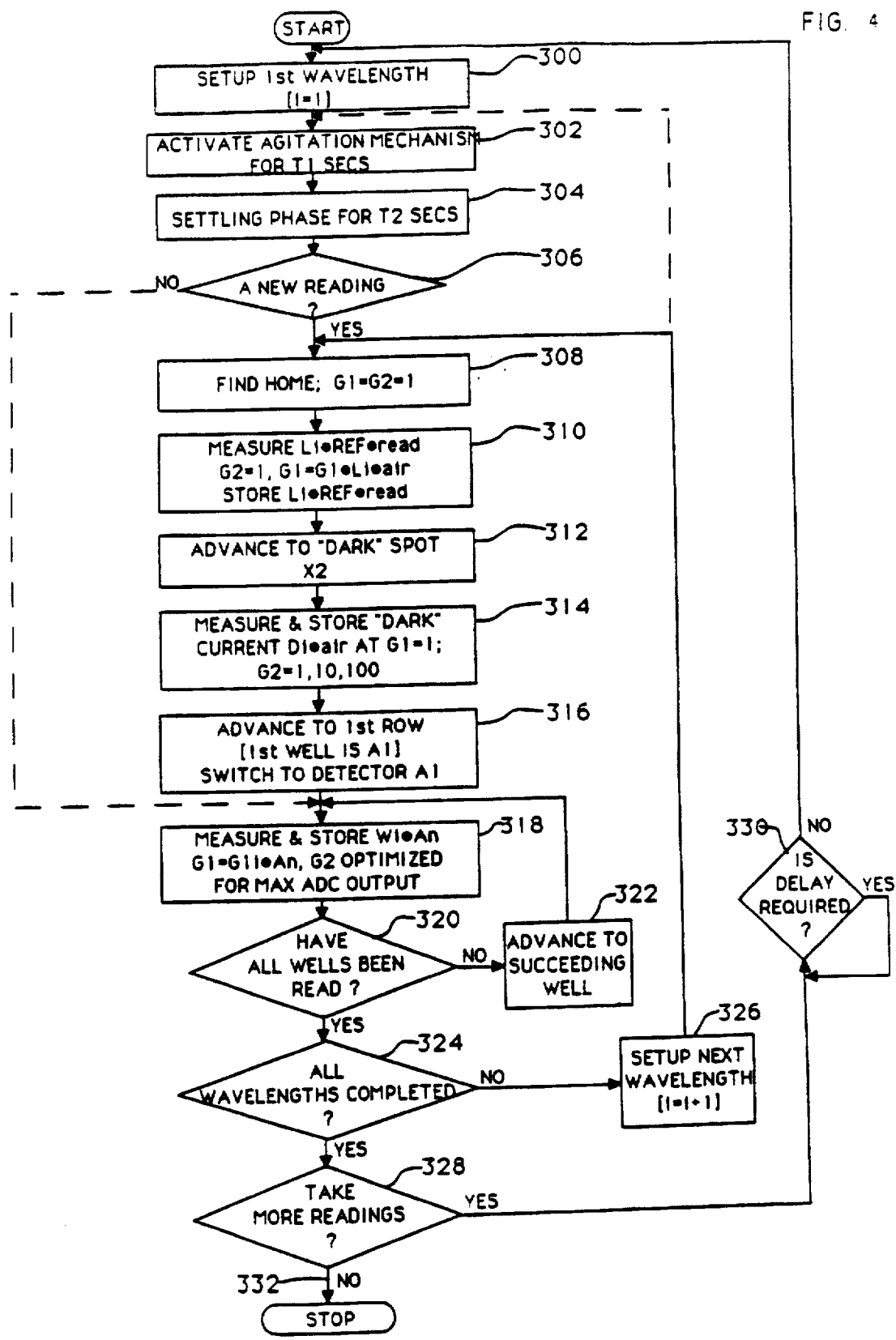

One embodiment of a sequence of operations to perform kinetic reading of samples is shown in the flowchart of FIG. 4. During kinetic reading of samples, a plurality of readings are taken at each sample, in order to determine the rate of chemical reaction at each sample over time.

As shown in FIG. 4, the operation steps of the endpoint assay of FIG. 3 arc utilized in conjunction with an additional loop, which includes steps 328 and 330. Following a positive determination step at 324, i.e. that all wells have been read at all the specified wavelengths, step 328 determines if it is desired to take an additional set of readings. If the answer at step 328 is positive, then step 330 is performed. Step 330 simply serves to provide a predetermined delay time between successive sets of readings. Such time delay may be a fixed time delay or, as previously described, may vary with time, for example by varying logarithmically with time. Following the time delay, if any, provided by step 328, step 300 et seq. are again performed in order to obtain a complete set of readings for the 96 samples in the multiple well plate. If the answer at step 328 is negative, then the step 332 is performed and no further readings are taken.

In one embodiment, the agitation prior to the initial set of readings is performed for about ten seconds, and subsequent agitations, performed before each subsequent set of readings, is performed for about three seconds. If desired, for each sample, analysis of rate of reaction is terminated upon a change of optical density (for example a change of approximately 0.200 OD), thereby providing data points only for the substantially linear portion of the reaction of each sample.

It will be noted from the above description that for any given sample well designated by the letter n, the gain G1 for the first stage variable gain amplifier 120 is individually determined for each sample well during the air calibration phase, and then is maintained constant for all subsequent readings in that kinetic reading cycle. The value of G1 is not adjusted again until the next air calibration phase. The gain $G2_a$ for the second stage variable gain amplifier is set equal to unity for all air reference and light reference readings, so that the dynamic range of the second stage amplifier 130 is utilized only when actual transmittance readings are being taken, and not for air reference readings.

Once the optical parameters defined and described above with respect to FIGS. 2, 3 and 4 have been obtained by the measurement system for a given sample well, the calculation of the optical density OD of the reacting sample contained within that sample well is calculated as:

$$OD_a = LOG_{10}[(W.AIR_n - D_{air})/(W_a - D_a) \times (L.REF_{read} - D_{read})/L.REF_{air} - D_{air}) \times (G2_a)]$$

This equation represents the logarithmic value of the product of three separate quantities. The first quantity $(W.AIR_a - D_{air})/(W_a - D_a)$ is the ratio of the adjusted signal readings for a given sample well (1) without any sample and (2) with a sample. All readings measured by the processing circuitry of the microprocessor system are adjusted for any offset voltages generated by the analog-to-digital converter or other system offsets and drifts by taking into account the corresponding dark current readings, as indicated in the above equation for $OD_a$. For instance, the signal reading $W.AIR_a$ is normalized for dark current effect by subtracting from it the value $D_{air}$ of the corresponding dark current reading. Similarly, this signal reading $W_a$ is adjusted by subtracting from it the corresponding dark current reading $D_a$.

The second quantity $(L.REF_{read} - D_{read})/L.REF_{air} - D_{air})$ is a measure of the ratio of the light reference readings obtained for a given sample well during the air calibration phase and the read phase. These two readings are also normalized on the basis of the corresponding dark current readings.

Finally, the third quantity (G2) in the above equation accounts for the effect of the dynamic ranging procedure described above, i.e., this quantity accounts for the effects of amplification of the signal readings by the processing circuitry.

The application of the above equation to the parameters measured as part of the kinetic reading cycle results in a highly accurate optical density measurement because the equation takes into account the effects of system offset voltages as well as those resulting from localized differences in light intensity and measurement conditions from one kinetic reading cycle to another, or from one sample well to another.

In accordance with a further feature of this invention, the computation of the logarithms required to calculate the optical density readings is performed by storing all the required logarithmic values within the microprocessor system in the form of a look-up table and subsequently using the digitized output of the processing circuitry as an index to retrieve the appropriate logarithmic value. In previous systems, the output signals of the photodetectors of the detector board have been fed to a logarithmic amplifier to obtain the logarithmic values of the output signals. This technique is subject to a variety of problems and limitations because of the constant need to adjust the system for offset gains of the logarithmic amplifiers. In addition, any temperature drift in the computing hardware must be accurately tracked and appropriately compensated to retain the accuracy of computation. According to the present invention, the computation of the logarithmic values is made substantially more accurate and independent of the system hardware parameters by storing within the microprocessor system memory all possible logarithmic values that would be required by the system in order to compute the optical density readings.

Figure 5:
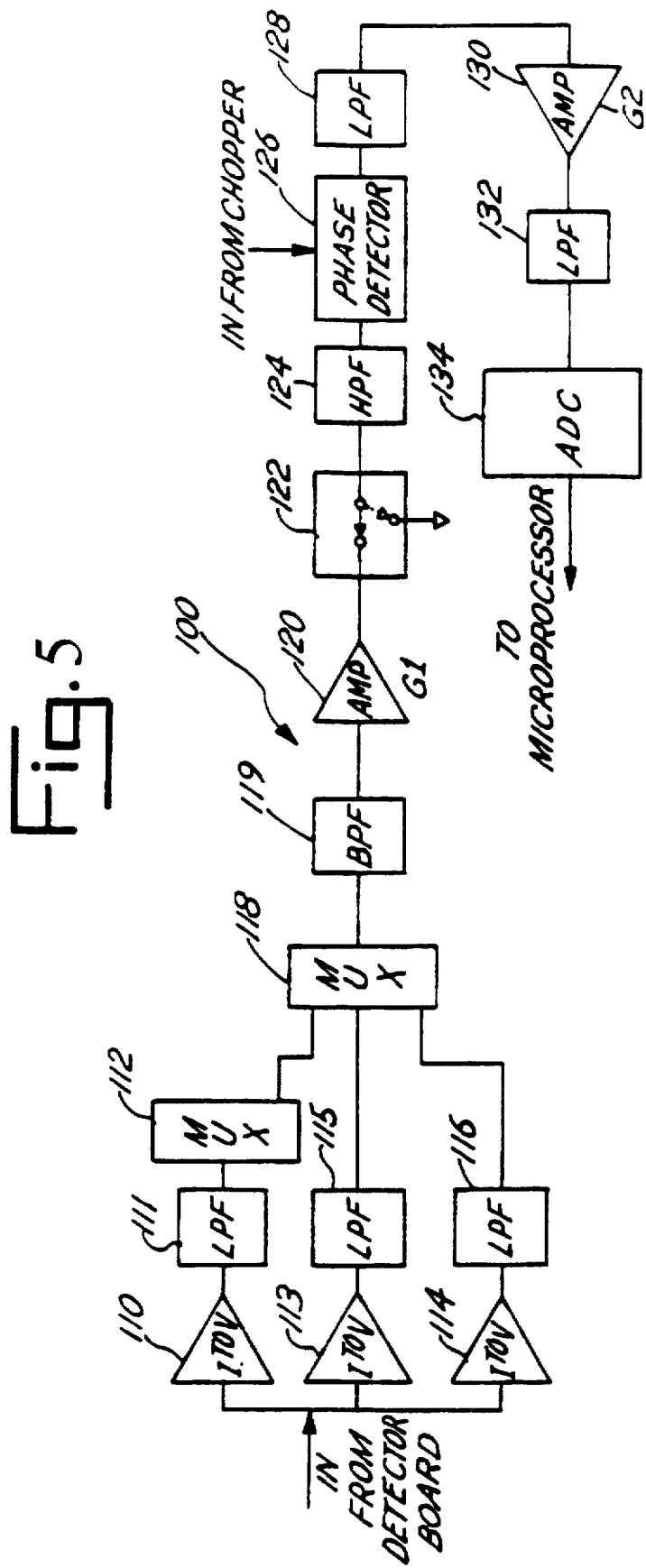
FIG. 5 is a flow diagram, described in and the same as FIG. 4 of U.S. Pat. No. 4,968,148.

More specifically, the look-up table contains logarithmic values corresponding to each of the possible outputs quantization levels for the analog-to-digital converter of the system (as shown in FIG. 5). Considering, for example, the case of a 12-bit supply analog-to-digital converter, the possible quantization levels range from 0 to 4095. This means that there are 4096 different values that a signal may take after it has been detected, processed and digitized. The logarithmic value corresponding to each of these 4096 possible values (except value 0, which denotes an error) are stored within a logarithmic look-up table which is contained within a ROM portion of the microprocessor system. The logarithmic look-up table is defined in such a way that the digitized output from the analog-to-digital converter serves as the address or index that points to the corresponding logarithmic value stored within the look-up table.

Because the look-up table is available within the microprocessor system memory, computation of the optical density becomes a simple matter of using the digitized output to extract the corresponding logarithmic value stored within the look-up table, and then performing simple mathematical subtractions.

The final computation step is to calculate the ratio of the OD values for each sample well on the microplate. As in the case of a dual wavelength read, each OD value is calculated by the microprocessor and saved in its memory. After all the sample wells are read at the specified wavelengths, the microprocessor will recall them for use in the ratio equation implemented. In this example the following equation is used.

$$R_a = OD_1/OD_2$$

where:

$R_a$ is the ratio of optical densities at two different wavelengths for sample well number n (n is the number of a sample well, between 1 and 96).

$OD_1$ is the OD value calculated for sample well number n at the first wavelength selected.

$OD_2$ is the OD value calculated for sample well number n at the second wavelength selected.

Both of these values are then recalled from memory by the microprocessor, and used to calculate the ratio for each sample well and reported. The ratio may be reported directly for each well and each scheduled measurement time. Alternatively, the microprocessor may calculate and report instead the $Log_{10}$ of each ratio, i.e. $Log_{10} R_n$. It is understood that the invention is not limited to the calculation of OD ratios at just two different wavelengths, but can be used to calculate OD ratios at more than two wavelengths selected as described below by example.

EXAMPLE 1

The following is a description of the preparation of buffer solutions. A first buffer system-pH indicator pair has been developed to precisely monitor well to well temperature fluctuations in microplate. Measurements of this temperature indicating solution are recorded as a ratio of the optical densities at 590 nm and 420 nm (in microplate readers) and 588 nm and 430 nm (in a diode array spectrophotometer).

Furthermore, a second buffer solution has been developed for use as a reference solution for the initial calibration of a microplate reader/spectrophotometer.

Materials:

| | |
|---|---|
| PIPES (Piperazine-N,N'-bis-[2-ethanesulfonic acid]) FW = 302.4 | $C_8H_{18}N_2O_6S_2$ |
| Sodium Phosphate Monobasic FW = 137.99 | $NaH_2PO_4.H_2O$ |
| Ethylenediamine, 99+% FW = 60.10 | $H_2NCH_2CH_2NH_2$ |
| BCP, i.e., Bromocresol Purple (5,5'-Dibromo-o-cresolsulfonphthalein) sodium salt | Anhydrous Mol Wt = 562.2 |
| Sodium Azide FW = 65.02 | $NaN_3$ |

Method of Preparation of Temperature Indicating Solution:

1. Prepare 50 mM solution of ethylenediamine.
2. Add 1.8× BCP (1×=60 mg/L) for optimal readings using a microplate reader and 0.9× for optimal readings using a 1.0 cm path length.
3. Add $5 \times 10^{-4}$ M Sodium Azide.
4. pH to 5.91 at 25° C.

Method of Preparation of Reference Solution:

1. Prepare 50 mM solutions of sodium phosphate monobasic and PIPES.
2. Add 1 part PIPES to 3.14 parts sodium phosphate monobasic.
3. Add 1.8× BCP (1×=60 mg/L) for optimal readings using a microplate reader and 0.9× for optimal readings using a 1.0 cm path length.
4. Add $5 \times 10^{-4}$ M Sodium Azide.
5. pH to 5.80 at 25° C.

When using a spectrophotometer, the solutions are poured into a cuvettes (containing a stir bar) with a 1.0 cm path length and allowed to equilibrate to a specified temperature. The temperature is recorded using preferably a thermistor thermometer. Usually, five different temperatures are measured for the calibration curve (e.g., 20° C., 25° C., 30° C., 35° C. and 40° C.). The optical density, subtracting a $H_2O$ blank, at 588 nm and 430 nm wavelengths are recorded at each temperature. The data are then converted to the form of results as shown in FIG. 9 by standard handling and graphic techniques.

EXAMPLE 2

When using a microplate reader, the temperature indicating solution was pipetted into row A and the reference solution into row B of the same flat bottom 96 well microplate at 200 uL. The microplate is allowed to equilibrate for approximately 20 minutes within a THERMOmax™ microplate reader. Consecutive readings of optical densities, after subtracting a $H_2O$ blank, at 420 nm–750 nm, 590 nm–750 nm, and 600 nm–750 nm are measured at room temperature. After the first reading, the incubator is set for 25° C. Again, the plate is allowed to equilibrate for approximately 20 minutes once the air in the incubator has reached the set temperature. The same measurements are again taken. The same procedure is followed at set temperatures of 30° C., 35° C. and 40° C.

Figure 10:
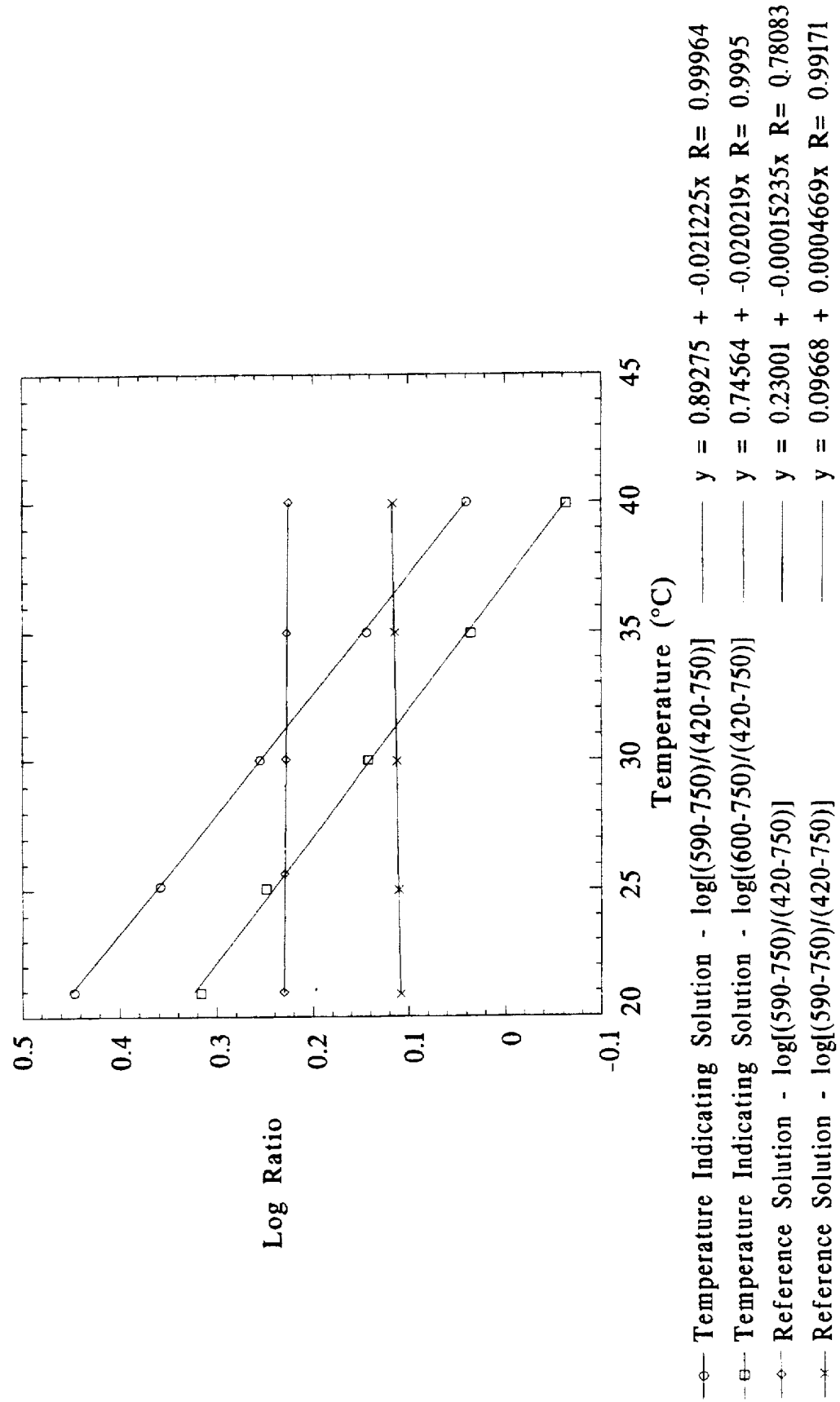
FIG. 10 is a graph showing the data obtained in Example 2.

The data are then transported outside of the microplate reader for the calculation of the ratios, but the instrument could be modified to make such a calculation internally. First, two ratios are calculated for each well at the various wavelengths: (590–750)/(420–750) and (600–750)/(420–750). Then, the average ratios for the eleven wells within the row, for both solutions, at the various temperatures are calculated. The log of the average ratio at each temperature (for both ratios and solutions) is then plotted and fitted by linear regression. The results are shown in FIG. 10.

The plots of $Log_{10} [(OD_{590}-OD_{750})/(OD_{420}-OD_{750})]$ vs. temperature, or alternatively, $Log_{10} [(OD_{600}-OD_{750})/(OD_{420}-OD_{750})]$ vs. temperature are both linear with identical slopes, within experimental error. The reference solution has a slope of near zero and the temperature-indicating solution has a slope of 20.2–21.2 milliPH/°C.

In the above demonstrated preferred procedure, a first and a second wavelength, $\lambda_1$ and $\lambda_2$ respectively, are chosen near the absorption maximum of the acidic and basic species of the pH indicator dye (420 and 590 nanometers, respectively, for the Bromocresol Purple example given above). A third wavelength, $\lambda_3$ is chosen where the pH indicator has no appreciable absorbance. The ratio $(OD\lambda_2-OD\lambda_3)/(OD\lambda_1-OD\lambda_3)$, or its reciprocal, is measured and the temperature change is proportional to the base 10 logarithm of the ratio, i.e.:

$$\text{Temperature} = (Log_{10} \text{Ratio} - A)/M \quad (1)$$

where A and M are constants and where the Ratio is $(OD\lambda_2-OD\lambda_3)/(OD\lambda_1-OD\lambda_3)$, or alternatively, the ratio is $OD\lambda_2/OD\lambda_1$. The $OD\lambda_3$ value helps to correct for light scattering errors. When light scattering is not a significant problem, $OD\lambda_3$ may be neglected and the simpler ratio may be employed in Equation (1). Although any base logarithm may be employed, once selected, the same base should be employed consistently so that constants A and M remain fixed for any defined temperature-indicating system. Base 10 logarithms are preferred as a matter of convenience.

If the relative temperature change is desired, e.g., the change in temperature is to be monitored over time, then the constant A in Equation (1) also may be neglected. For example, temperature changes measured over time, (t), are given as, $$\text{Temp}(_{t2}) - \text{Temp}(_{t1}) = [Log_{10} \text{Ratio}(_{t2}) - Log_{10} \text{Ratio}(_{t2})]/M \quad (2)$$

Alternatively, if absolute temperature is desired, the constant A in Equation (1) may be evaluated, by measuring both the temperature and $Log_{10}$ Ratio. This evaluation may be performed only once at the time of manufacture of the temperature-indicating solution. For such measurements of absolute temperature, however, an additional problem exists, as shown in FIG. 10, in that a wavelength error (shown as determination of $OD_{600}$ instead of $OD_{590}$ for one of the two pairs of curves of identified slope) results in a change in constant A of Equation (1) (i.e. the intercept) but no change in constant M (i.e. the slope). Thus, a miscalibration of the wavelength in the spectrophotometer, or microplate reader, would result in an error in measurement of absolute temperature change. Such an error, however, could be corrected by monitoring, at identical wavelength settings, the ratio of optical densities, of a reference solution, which similarly has been calibrated at time of manufacture. As shown in FIG. 10, the plots of $Log_{10}$ Ratio of the temperature-indicating solution, using either $OD_{600}$ or $OD_{590}$ to calculate the ratio, have identical slope, to within experimental error, but have non-identical Y-intercepts. Similarly, the plots of $Log_{10}$ Ratio of the reference solution, using either $OD_{600}$ or $OD_{590}$ to calculate the ratio, have nearly zero slope but also have non-identical Y-intercepts. To within experimental error, the difference in the intercepts for the reference solution equal the difference in the intercepts for the temperature-indicating solution. Thus, the intercept difference for the reference solution may be used to correct for determinate error in the temperature-indicating solution caused by an incorrect wavelength setting of the spectrophotometer or microplate reader.

An example procedure for absolute temperature measurement employing the temperature-indicating solution and the reference solution compositions given above, and $OD_{590}/OD_{420}$ as the ratio, is as follows:

Standardization

Measure the $Log_{10}$ Ratio of the temperature-indicating solution in a spectrophotometer at 25° C. and again at 36° C. For example, it is found that $Log_{10}$ Ratio=0.590–0.0182 T (°C). (Store the values 0.590=A; and –0.0182/°C.=M.)/

Measure the $Log_{10}$ Ratio of the reference solution in a spectrophotometer at 25° C. and again at 36° C. For example, it is found that $Log_{10}$ Ratio=–0.068 +0.00003 T (°C). (Store the value B'=–0.068.) The slope+0.00003/°C. may be neglected for all measurement between 0° C. and 100° C.

Measurement of Unknown Temperature

With a selected spectrophotometer, photometer, or microplate reader, measure the $Log_{10}$ Ratio of the reference solution at any temperature between 0° C. and 100° C. In the present example, this value was found to be –0.070 for a selected instrument. (Store the value $B'_x$=–0.070).

The temperature of the temperature-indicating solution may be monitored with the same instrument and wavelength setting by measuring the $Log_{10}$ Ratio of the temperature-indicating solution at any temperature between 0° C. and 100° C. where the temperature may be calculated from Equation (3):

$$\text{Temperature (°C.)} = \frac{(\text{Log}_{10} \text{ Ratio} + (B' - B'_x) - (A)}{M} \quad (3)$$

In this above example, the temperature of the temperature-indicating solution was $$\text{Temperature (°C.)} = \frac{(\text{Log}_{10} \text{ Ratio} + [-0.068 - (-0.070)] - (0.590)}{0 - 0.0182/°C.}$$

or, $$\text{Temperature (°C.)} = \frac{(0.588) - \text{Log}_{10} \text{ Ratio})}{0.0182/°C.}$$

For example, an experimentally determined value of $Log_{10}$ Ratio=0.100 for the temperature-indicating solution would indicate a temperature of 26.81° C.

EXAMPLE 3

The following shows the use of a ratiometric absorbance method to kinetically monitor the rate of extracellular acidification caused by CEM cells. The cells are suspended in physiological medium containing phenol red as the pH indicator dye. The medium and cells are retained in individual wells of a microplate maintained in a 37° C. chamber of a microplate reader. The contents of the microplate wells are mixed by oscillatory motion of the microplate for a predetermined time prior to each of repetitive measurements of the $Log_{10}$ [optical density at 560 nanometers/optical density at 420 nanometers]; this parameter is abbreviated as Log R. The slope of each plot of Log R vs. time yields the rate of extracellular acidification in each well of the microplate.

The medium used for these measurements is formulated so that Log R is unaffected by changes in temperature which occur upon placing the microplate in the 37° C. chamber. The medium is based upon a modified RPMI 1640 obtained from Irvine Scientific, Santa Ana, Calif., Catalog No. 98276. The modified RPMI 1640 medium contains, in addition, 1.25 mM sodium phosphate, pH 7.04, 0.531 mM phenol red and 1000 units/liter penicillin, as penicillin G, and 1 mg/liter streptomycin, as streptomycin sulfate. The medium formulation is shown in Table 1.

The CEM cells (CEM-CM3, human acute lymphoblastic leukemia) may be obtained from the America Type Culture Collection, Rockville Md. and are grown under 5% $CO_2$ in complete RPMI 1640 medium, with 10% fetal bovine serum (complement heat inactivated), 10 mM HEPES buffer and 1000 units/liter penicillin, as penicillin G, and 1 mg/liter streptomycin, as streptomycin sulfate. The cells are then centrifuged at 5° C. and resuspended to $5 \times 10^6$ cells per ml in the indicator medium shown in Table 1 and stored on ice. To begin the measurement, 60 μl of the cells were added to the wells of a flat-bottom, 96-well polystyrene microplate. To some wells 60 μl of medium without cells was added.

THERMOmax™ microplate reader, set to 37° C., with Automix™ on, and SOFTMAX® software (Molecular Devices Corporation, Menlo Park, Calif.) and an Apple™ MacIntosh™ computer were used to kinetically monitor the optical density changes. The ratio of optical density at 560 nanometers/optical density at 420 nanometers, as a function of time, was measured by using the $OD^{\lambda 1} - OD_{\lambda 2}$ feature of a THERMOmax™ microplate reader modified to measure $OD_{\lambda 1}/OD_{\lambda 2}$ instead of $OD_{\lambda 1} - OD_{\lambda 2}$ (as described previously).

Figure 11:
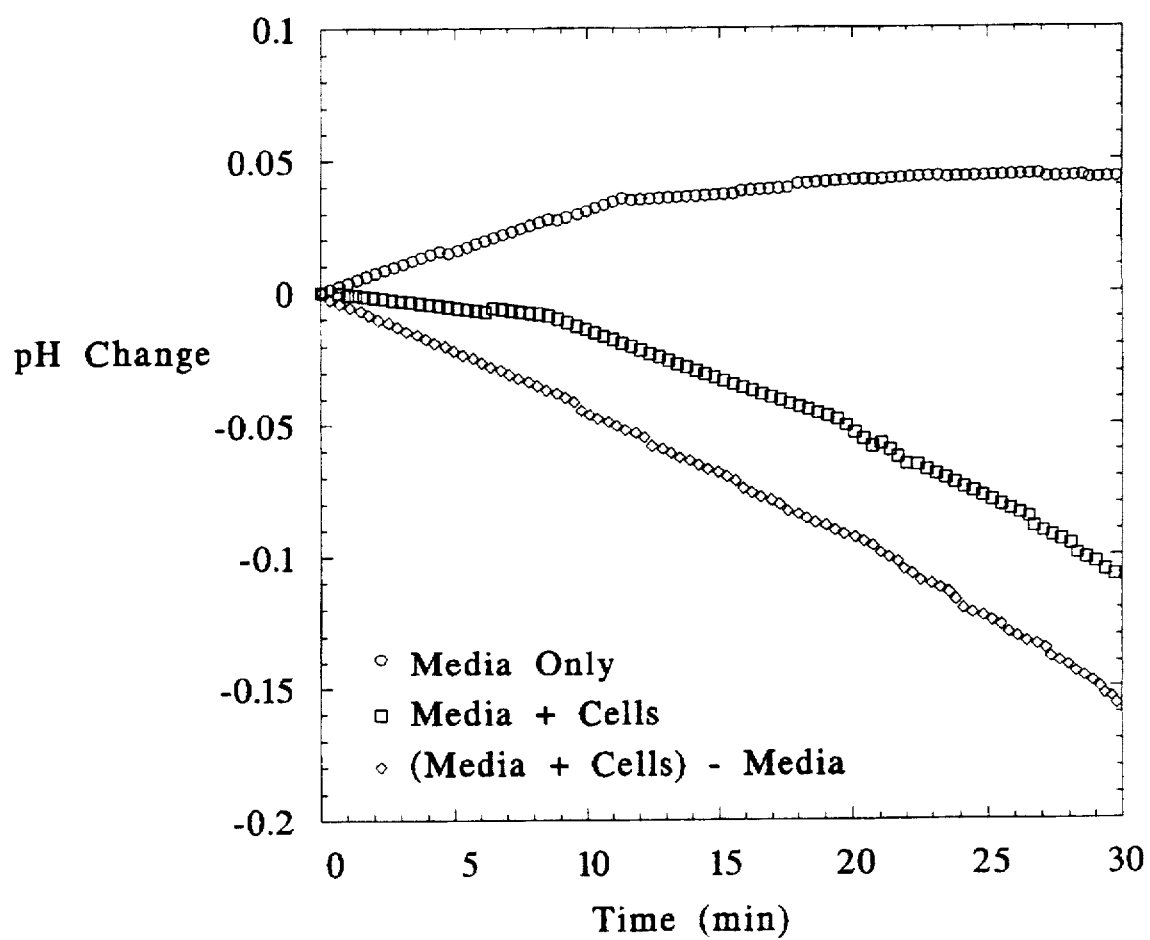
FIG. 11 is a graph further described in Example 3 of extracellular acidification by CEM cells.

The $\log_{10}$ of the ratio of optical densities at 560 nm/420 nm was calculated and plotted as a function of time. FIG. 11 shows the $\log_{10}$ of the ratio of optical densities at 560 nm/420 nm (i.e. the pH change), plotted as a function of time after placing the microplate into the 37° C. chamber. The data from two representative wells containing the medium alone and the medium with CEM cells is shown. As the cells are warmed from room temperatures to 37° C., the rate of pH change increases. In the well without cells a 0.04 pH unit apparent increase in pH was observed as the medium was warmed to 37° C. This small apparent change in pH without cells, may have been due to either a small remaining temperature dependence of the buffer indicator system or alternatively due to degassing of ambient dissolved $CO_2$ resulting in a small increase in pH as the temperature is increased. The best estimation of the true rate of pH change caused by the cells, therefore, is the difference between the two lines, i.e. the pH change in medium with cells minus the pH change in medium alone, shown as the lower line in FIG. 11.

A summary of the steps taken to carry out the method is as follows:

Preparation of Low-Buffer Media:
1) Prepare a volume of Low-Buffer RPMI (98276 Deficient RPMI 1640 -Irvine Scientific, Santa Ana, Calif.) with 40× phenol red from 27.6 mM stock solution (2000×).
2) Add a total of 1.25 mM phosphate using a ratio of 3.8019:1 (dibasic:monobasic).
3) pH of solution=7.04

Preparation of CEM cells in solution:
1) Spin down cells and remove old media.

2) Resuspend cells in approximately 7 mL cold low-buffer media.
3) Spin down the cells at 5° C. and again remove media.
4) Resuspend cell in low-buffer media so that there are $5 \times 10^6$ cells/mL.

Procedure:
1) Pipet 60 microliters of low-buffer media into rows C and D of a flat bottom microplate.
2) Pipet 60 microliters of media containing the cells in suspension into rows E and F of the same microplate.
3) Measure the ratio of optical density at 560 nm/optical density at 420 nm (using the ratiometric microplate reader described previously) kinetically for one hour with Automix™ on and incubator set at 37° C.
4) Data was transported into Excel® with an Apple™ MacIntosh™ II Computer for calculations.
5) Plot pH change vs. time (min). See FIG. 11.

The modified RPMI 1640 medium given in Table 1 is preferred for measuring extracellular acidification of mammalian cells under conditions where optimal nutrients are supplied for cell growth. Other appropriate media supporting growth of mammalian cells alternatively may be used, including, but not limited to AIM V® Media, Basal Media Eagle, $BGJ_b$ Medium, CHO-S-SFM, CMRL Media, Dulbecco's Modified Eagle Medium, DMEM/F-12, Fischer's Media, Glasgow Minimum Essential Media, Iscove's Modified Dulbecco's Medium, Lebovitz's L-15 Media, McCoy's Media, Media 199, Minimal Essential Media, NCTC Media, F-10 or F-12 Media, OptiMEM® Protein-Free Hybridoma Media, Neuman & Tytell's Media, Trowels's Media, Waymouth's Media, and William's Media.

Other types of cells may employ other types of media. For example, amphibian cells may employ Wolf & Quimby's amphibian Culture Medium or other media suitable for amphibian cells. For insect cells, for example, media include Grace's Insect Cell Culture Media, IPL-41, Schneider's Drosophila Medium, Sf-900, or TC-100 Media.

Other types of cells, either eucaryotic or procaryotic, may employ other suitable media optimized for cell growth. In each case, however a pH indicator dye will be added to the media. To further optimize the composition of the medium for monitoring extracellular acidification by optical methods, however, the concentration of one or more buffering species preferably will be adjusted, or one or more buffering species will be added to the media so that absorbance of the indicator dye will not change substantially with a change in temperature of the medium.

EXAMPLE 4

Alternatively, very simple media may be used to monitor extracellular acidification by biological cells. Preferably, simple media will be used for measurements performed over short periods of time ranging from less than one minute to 24 hours, where cell growth is not required. In general, the media for monitoring extracellular acidification will be composed of selected pairs of at least one pH indicator dye and at least one buffer system.

Figure 12:
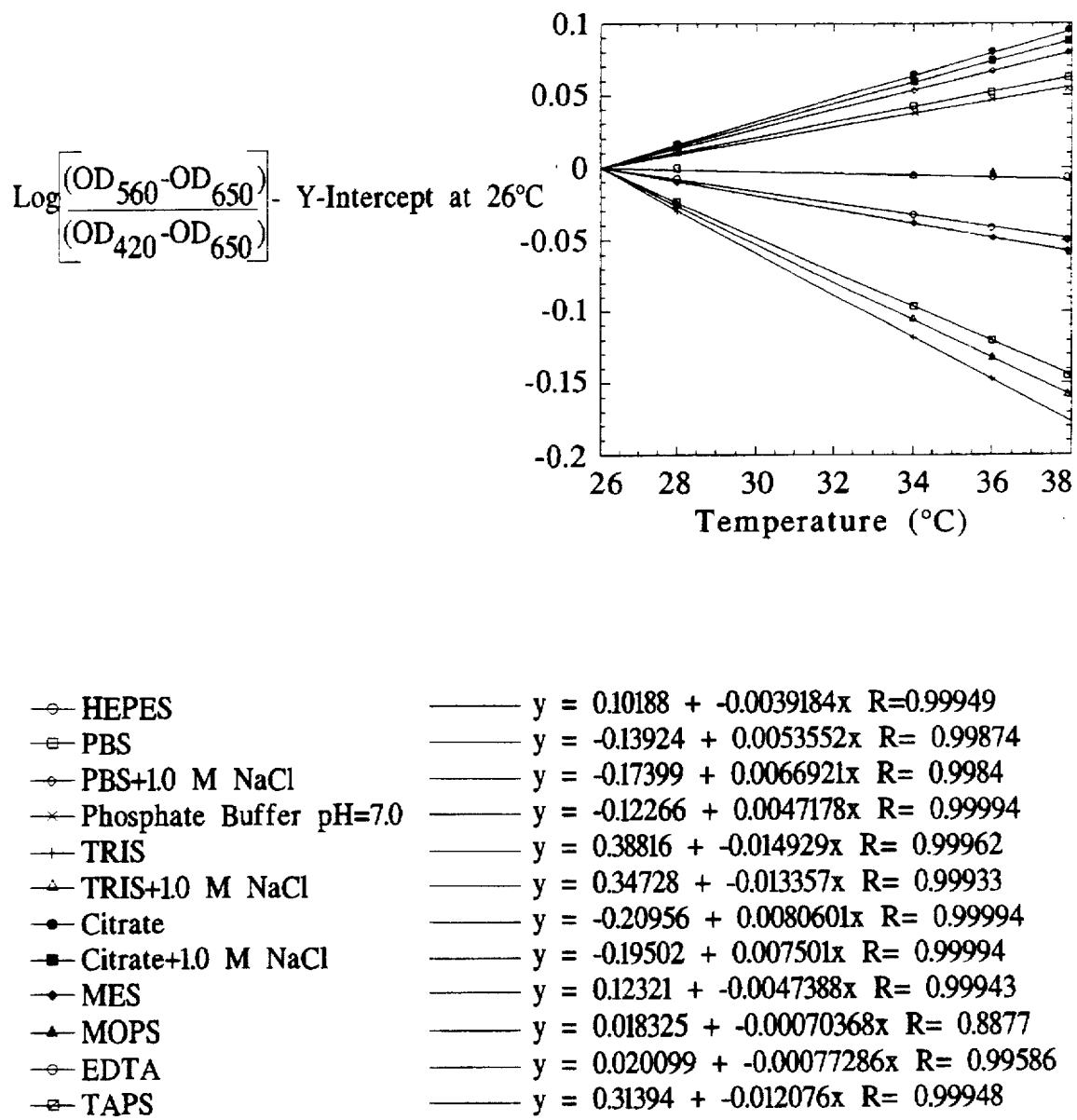
FIG. 12 is a graph, further described in Example 4, of temperature sensitivity of various pH buffer systems and phenol red pH indicators, as pairs.

FIG. 12 shows the apparent change in pH with change in temperature of various buffering systems, as indicated by the pH indicator dye phenol red. Unless denoted otherwise, all buffering species are present at 50 mM total concentration, either as the free acid with the sodium salt or as the free base with the chloride salt. Each of the buffering systems is in equilibrium with $CO_2$ naturally present in air at atmospheric pressure.

As shown in FIG. 12, both the MOPS (3-[N-Morpholino] propanesulfonic acid) and the EDTA (Ethylenedinitrilo-Tetraacetic Acid) buffers, when paired with the Phenol Red pH indicator, result in very little, optically apparent, pH change with change in temperature. In both cases the indicated pH change was less than 1 millipH/°C. The Citrate buffer resulted in 750 millipH/°C., and with 1.0M NaCl added resulted in 8.06 millipH/°C. The PBS (Phosphate Buffered Saline, 120 mmol/L NaCl, 2.7 mmol/L KCl, 10 mmol/L Phosphate Buffer, pH=7.4) resulted in 5.36 millipH/°C., and with 1.0M added NaCl resulted in 6.69 millipH/°C.

The Phosphate Buffer (0.05M Potassium Phosphate Monobasic-Sodium Hydroxide, pH 7.0) gave 4.72 millipH/°C. apparent change in pH. The HEPES (N-[2-Hydroxyethyl]piperazine-N'-[2-ethanesulfonic acid]) buffer system gave –3.92 millipH/°C. apparent change. The MES (2-[N-Morpholino]ethanesulfonic acid) buffer system gave –4.74 millipH/°C. apparent change in pH. The TAPS (3-{ [tris-(hydroxymethyl)-methyl]-amino }-propanesulfonicacid)buffer system gave –12.07 millipH/°C. apparent change in pH. The TRIS (tris[Hydroxymethyl] aminomethane) buffer system gave –14.93 millipH/°C. apparent change in pH, and with added 1.0M NaCl gave –13.36 millipH/°C. apparent change in pH.

As shown in FIG. 12, both the MOPS and the EDTA buffers, when paired with the phenol red pH indicator, result in very little, optically apparent, pH change with change in temperature. Thus either the MOPS or the EDTA buffer systems would be suitable for use with the phenol red pH indicator. Often, however, it is desirable to incorporate buffering species, such as phosphate or carbonate, because biological cells may require such buffering species for optimal response to a biological response modifier or a cellular agonist, such as a hormone or a drug. If all significant buffering species are known, we have found that the following general formula may be applied as a general method to make a complex buffer (i.e. one with two, or more, buffer systems) that has minimal optically indicated change in pH with change in temperature.

$$\Sigma \beta_1 M_1 + \beta_2 M_2 + \beta_3 M_3 \ldots \beta_n M_n = 0) \qquad (4)$$

where, $\beta_1$, $\beta_1$, $\beta_3$, and $\beta_n$ are the buffering capacities of the first, second, third, and nth buffering systems, respectively, and $M_1$, $M_2$, $M_3$, and $M_n$ are the slopes (e.g. millipH/°C.) of individual plots of optically-apparent pH change with temperature for the individual buffer system-pH indicator pairs. Examples of such plots are shown in FIG. 12.

Thus, the buffering system-pH indicator dye pairs may comprise single buffering species or, preferably, will have two, or more, buffering systems. The two, or more buffering systems are chosen such that a first buffering system produces an apparent increase in pH when temperature is elevated (as indicated by the chosen pH indicator dye) and a second buffering system produces an apparent decrease in pH when the temperature is elevated. The first and second buffering systems are combined in the proper proportions so to provide cancelling of the temperature effect on the apparent pH. That is, when the two, or more, buffering systems are combined in proper proportion, no substantial apparent change in pH is produced when the temperature is varied.

The proper ratio of the concentrations of each buffering species may be chosen as described above or alternatively determined experimentally by iteration. The iterative method employs successive measurements of apparent pH change with changing temperature while adjusting the ratio of the concentrations of the two or more buffer systems until a satisfactory result, i.e. very little optically apparent pH change with change in temperature, is achieved. One of the two or more buffer systems may be the H₂CO₃/bicarbonate/carbonate buffer system. Because of the presence of CO₂ in the atmosphere and in the respired gases of aerobic cells, this buffering system is usually present in significant amount in biological media between the pH values of 6.0 and 10.0.

EXAMPLE 5

Figure 13:
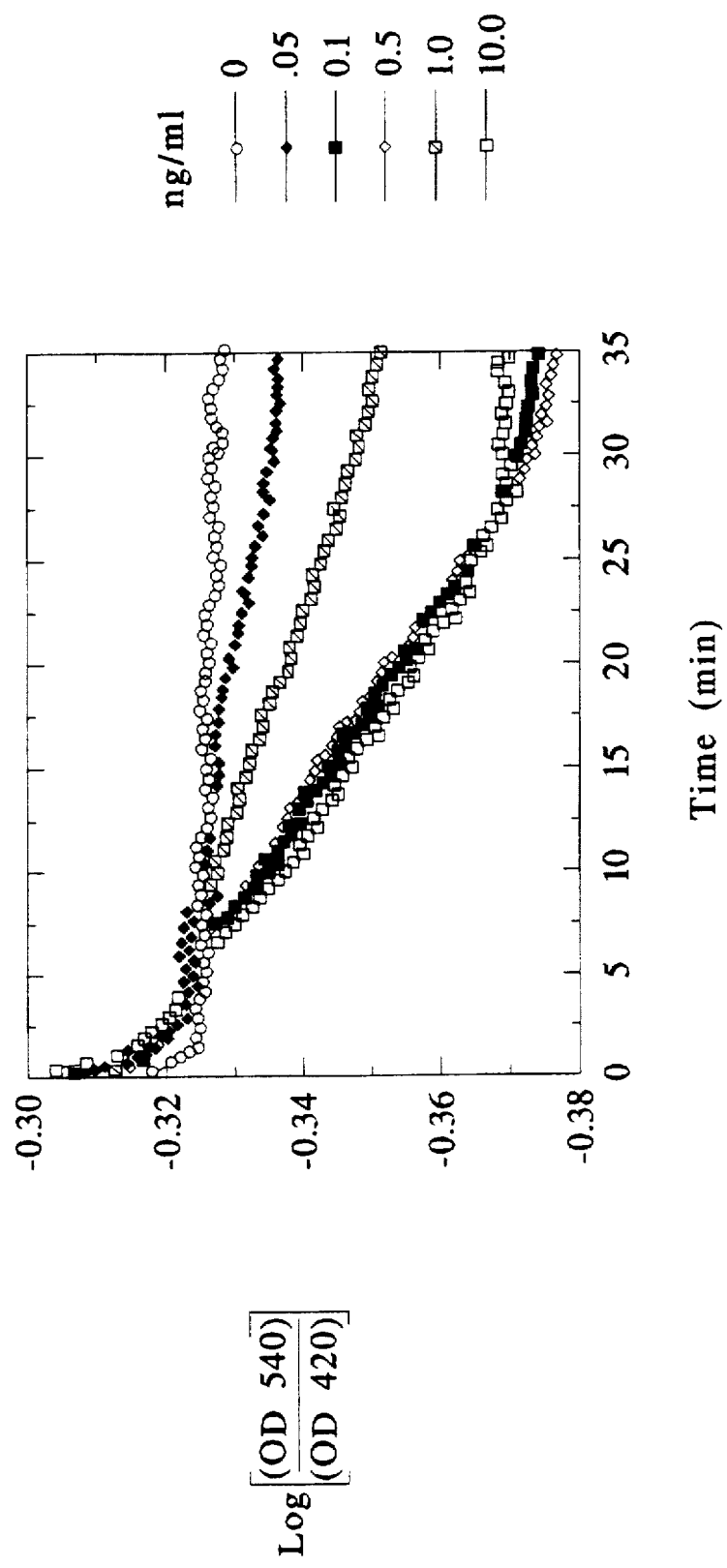
FIG. 13 is a graph, further described in Example 5, of GM-CSF Dose Response using TF-1 Cells.

The results from using a preferred simple media (shown in Table 2) to monitor extracellular acidification by TF-1 cells is shown in FIG. 13. The TF-1 cells and are grown in complete RPMI 1640 medium with 2.0 mM L-glutamine (Catalogue No. 430-1800, GIBCO-BRL, Grand Island, N.Y.) with added 100 mM sodium pyruvate, 50 μM β-mercaptoethanol, 1000 units/liter penicillin and 1.0 mg/liter streptomycin, 10% fetal bovine serum and Ing/ml GM-CSF (human Granulocyte/Macrophage—Colony Stimulating Factor) under 5% CO₂ at 37° C.

The cells are maintained at between 5×10⁵ cells per ml and 5×10⁶ cells per ml. Eighteen to twenty four hours prior to measuring extracellular acidification, the cells are resuspended in medium without the GM-CSF. Just prior to measurement of extracellular acidification, the TF-1 cells are spun down and the old medium removed by aspiration. The cells are resuspended to 1×10⁶ cells/ml in the simple indicator medium shown in Table 2. The cells are maintained in this medium on ice prior to addition to microplate wells.

The extracellular acidification measurements were done in a flat-bottom, 96-well polystyrene microplate placed in a THERMOmax™ microplate reader, set to 37° C. The cells in 100 ul of medium were preheated to 37° C. for 20 minutes prior to adding 10 ul of medium to give a final GM-CSF concentration ranging from 0 to 10 ng/ml. Extracellular acidification was measured with Automix™ on, and with SOFTMAX® software (Molecular Devices Corporation, Menlo Park, Calif.) and an Apple® Macintosh™ computer were used to kinetically monitor the optical density changes. The ratio of optical density at 560 nanometers/optical density at 420 nanometers, as a function of time, was measured by using the $OD\lambda_1-OD\lambda_2$ feature of a THERMOmax™ microplate reader modified to measure $OD\lambda_1/OD\lambda_2$ instead of $OD\lambda_1-OD\lambda_2$ (as described previously). The $\log_{10}$ of the ratio of optical densities at 560 nanometers/optical density at 420 nanometers was calculated and plotted as a function of time.

Figure 14:
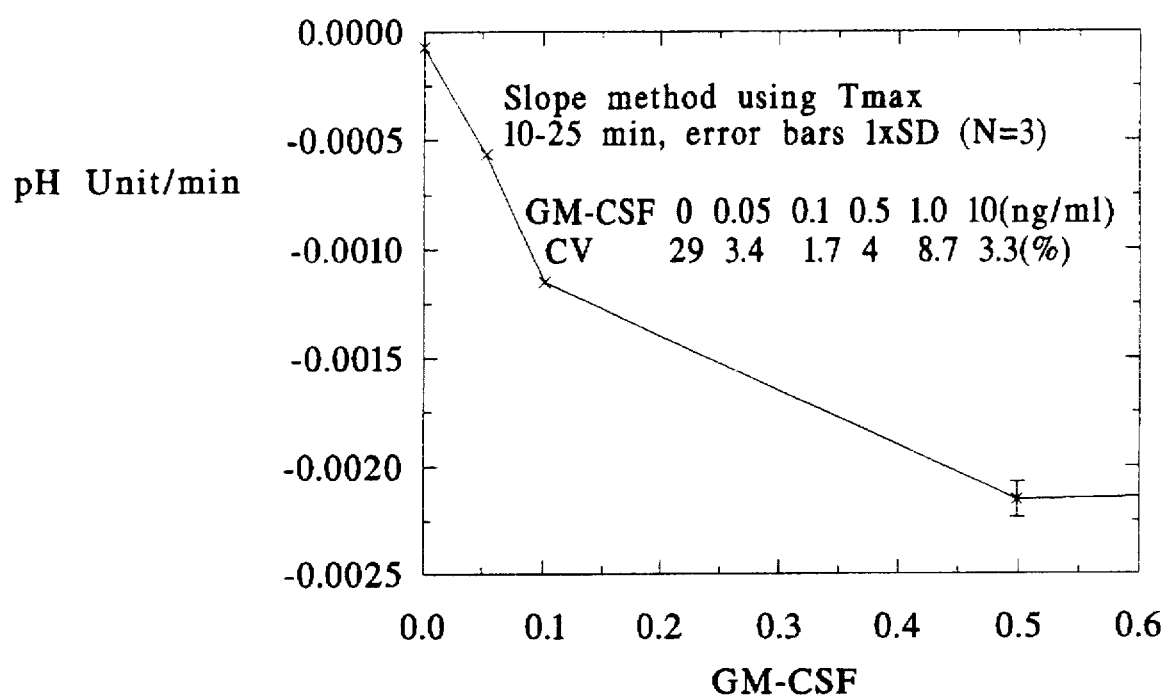
FIG. 14 is a graph, further described in Example 5, of GM-CSF Stimulation of TF-1 Cells.

The following shows the use of TF-1 cells and a method of using phenol red indicator to detect GM-CSF. Using 1×10⁵ cells in 10 ul per well, run in triplicate, the acidification rates between 10 and 25 minutes after adding GM-CSF varied from 0.06 to 2.1 millipH units/minute for cells treated with 0 to 10 ng/ml recombinant hGM-CSF (FIG. 14). There was no observance of a dose response at saturating levels of GM-CSF (greater than 0.05 ng/ml). Earlier work shows that approximately 1 ng/ml gives the optimum proliferation rate for TF-1 cells in culture.

The precision of the measurement was extremely high. At levels tested (0 and 10.0 ng/ml), the CV% for acidification rate varied from 2% to 4%. As shown in FIGS. 13 and 14, it is possible to use a method using phenol red in the THERMOmax™ microplate reader to quantitate GM-CSF in less than a 1 hour protocol using TF-1 cells. This method required a special low-buffering medium formulation, preheating the cells in the plate at 37° C. for 20 minutes prior to the addition of cytokine, automixing the wells prior to each ratiometric optical density measurement, and kinetically monitoring the cells for about 30 minutes.

In the preferred procedure a first and a second wavelength, $\lambda_1$ and $\lambda_2$, respectively, are chosen near the absorption maximum of the acidic and basic species of the pH indicator dye (420 and 540 nanometers, respectively, for the phenol red example given above). A third wavelength, $\lambda_3$ is chosen where the pH indicator has no appreciable absorbance. For phenol red, a preferred $\lambda_3$ is 650 nanometers. The ratio $(OD\lambda_2-OD\lambda_3)/(OD\lambda_1-OD\lambda_3)$, or its reciprocal, is measured and the rate of pH change is given as a base 10 logarithm of the ratio, i.e.:

$$dpH/dt = d\,\text{Log}_{10}[(OD\lambda_2-OD\lambda_3)/(OD\lambda_1-OD_3)]/dt \quad (5)$$

The $OD\lambda_3$ value helps to correct for light scattering errors, which tend to be especially significant when greater than 10⁵ cells are placed in each well of the microplate. When light scattering is not a significant problem, $OD\lambda_3$ may be neglected and the rate of pH change can be calculated more simply as:

$$dpH/dt = d\,\text{Log}_{10}[(OD\lambda_2/OD\lambda_1]/dt \quad (6)$$

EXAMPLE 6

Vertical beam absorbance readers have the disadvantage in that the light absorbing path length of a liquid sample is not fixed by the walls of a cuvette. Instead, a boundary of the light path is an air-liquid interface that is usually curved and of indeterminate shape. It is difficult to accurately determine the path length. It is also difficult to maintain the same path length during repetitive absorbance readings over time.

In order to accurately determine the path length, the following method may be used. The method uses a second chromophore, which is added to the sample in a known concentration. The chromophore to be determined in the measurement absorbs at wavelength ($\lambda_1$), the second chromophore absorbs at a second wavelength ($\lambda_2$). Preferably, the second chromophore does not absorb appreciably at wavelength ($\lambda_1$). For example, the second chromophore could be selected from a group of chromophores that have appreciable absorbance only in the far red or infrared wavelength range. An example of such a chromophore is copper phthalcyanine (Pigment Blue 15; molecular formula: $C_{32}H_{16}CuN_8$), which absorbs maximally at 795 nm.

During each repetitive determination of sample absorbance ($OD_{\lambda 1}$) at wavelength $\lambda_1$, the absorbance of the second chromophore ($OD_{\lambda 2}$) at wavelength $\lambda_2$ is also determined. If the concentration of the second chromophore is known, then the concentration of the first chromophore may be determined independent of path length, as shown below.

$$OD_{\lambda 1} = A_1 d C_1 \quad (7)$$

$$OD_{\lambda 2} = A_2 d C_2 \quad (8)$$

where $A_1$ is the absorption coefficient of the substance to be determined, d is the path length of the sample, $C_1$ is the unknown concentration of the substance to be determined, $A_2$ is the absorption coefficient of the second chromophore, and $C_2$ is the known concentration of the second chromophore. Rearrangement of the above expressions gives the expression for $C_1$ that is independent of the path length (d), as shown below.

$$C_1 = OD_{\lambda 1} A_2 C_2 / OD_{\lambda 2} A_1 \quad (9)$$

or $$C_1 = (OD_{\lambda 1}/OD_{\lambda 2})(A_2/A_1)C_2$$

Therefore, if $A_2$, $A_1$, and $C_2$ are known, $C_1$ may be determined independently of path length by measuring ($OD_{\lambda 1}/$ $OD_{\lambda 2}$). Also, the change in $C_1$ may be determined over time by measuring ($OD_{\lambda 1}/OD_{\lambda 2}$) over time. Thus, the measurement of $C_1$ will be unaffected by a variable length of light absorbtion path. This method also enables the determination of the exact length of light absorbtion path (see Equation 10) for each measurement and provides for proportionately correcting for any errors caused by any change in path length over time.

$$d=OD_{\lambda 2}/A_2 C_2 \qquad (10)$$

EXAMPLE 7

Various pH indicator dyes have different absorbance maxima when they are in either the protonated or the unprotonated state. An example of such a pH indicator dye is phenolsulfonephthalein (Phenol Red; molecular formula: $C_{19}H_{14}O_5S$).

The protonated form has an absorbance maximum at 423 nm (yellow) and the unprotonated form absorbs maximally at 557 nm (red). Independent of the path length of the sample, the ratio of absorbance at 557 and 423 nm will be a function of the pH of the sample.

With changes in the pH, the absorbance at one wavelength decreases while the other increases. Thus, the ratio of optical densities, at these two wavelengths, will change much more than the optical density at either of the two wavelengths. This method is a very sensitive method of measurement of pH as already demonstrated in Examples 3 and 5.

Various other colored indicators exist for measuring changes other than pH. For example, there are indicators for measuring redox potential, water content, carbon dioxide concentration, etc. As for Phenol Red, the indicators undergo a change in the spectrum of light absorbtion upon titration with the appropriate reagent. Thus, measurement of absorbance ratios at two wavelengths would also be useful for these types of measurements.

Table 3 shows examples of various pH and redox potential indicators that may be used with the disclosed invention. For mammalian cells, the pH indicators that are useful generally will have a $pK_a$, and hence change in absorbance spectrum, between the pH values of 6.0 and 8.0. Thus, the pH indicators listed from the Universal pH indicator through phenolphthalein will be most useful for mammalian cells. Phenol red is the preferred pH indicator for mammalian cells because its $pK_a$ is between 7.0 and 8.0 and also because phenol red has shown minimal toxicity toward most mammalian cells.

Other types of cells will require the use of pH indicators with a different range of $pK_a$ values. For example, monitoring the rate of extracellular acidification by acidophilic bacteria, or other organisms in acid media, will require the use of pH indicators with a lower $pK_a$, generally from 2.0 to 6.0, such as bromophenol blue, or its chloro-analogs. Alternatively, monitoring the rate of extracellular acidification by alkalinophilic bacteria, or other organisms in alkaline media, will require the use of pH indicators with a higher $pK_a$, generally from 8.0 to 12.5, such as indigo carmine or thymol blue.

In general, both the acidic and basic forms of the pH indicator, or reduced and oxidized forms of the redox potential indicator will be present as a charged ion, either a negatively-charged ion, or positively-charged ion. The charge performs two functions. First it helps to keep both forms of the indicator dye soluble in aqueous media. Secondly, the charge prevents the dye from rapidly entering the cells or intracellular organelles. By entering the cells or intracellular organelles the indicators could accumulate there, or alternatively, could act to discharge transmembrane pH gradients, or to discharge transmembrane redox potential gradients in the case of the redox potential indicator. In any of these cases, the indicator would have increased toxicity to the cells. Generally, the indicator, if negatively charged, will carry a sulfonic acid group, or if positively charged, will carry a quaternary amine group to insure that all forms of the indicator remain charged.

The indicator dyes preferably will have a different color in the basic and acidic forms, for the pH indicator; and for the reduced and oxidized forms, for the redox potential indicator; and for the hydrated and non-hydrated forms of the water indicator, etc. A single color, indicator, for example, phenolphthalein, will also work, however. The absorbance in the ultraviolet range could be used for the second wavelength, or alternatively, the change in pH could be followed optically at a single wavelength., e.g. for phenolphthalein at a wavelength near 550 nanometers. Similarly, for a redox potential indicator, such as methylene blue, absorbance at a wavelength near 660 nanometer is preferrable.

For measurements carried out in vertical-beam photometers, such as microplate readers, measurement at two wavelengths is especially advantageous, as mentioned previously, because of possible fluctuations in light path length. As mentioned previously, the errors resulting from these fluctuations may be eliminated by taking the ratio of at least two wavelengths. As mentioned previously, the optical density at the second wavelength may be constant, and unchanging, during the monitored reaction, or alternatively, may be changing in an opposite direction to the optical density at the first wavelength, as occurs for the pH indicator examples given above with e.g., phenol red or bromocresol purple. In either case, the effect of any change in light path length may be eliminated from the measurement.

EXAMPLE 8

The M1WT3 cells used for the following experiments were obtained from the American Type Culture Collection (No. CRL 1985). These cells were a line of CHO-K1 cells transfected with the gene for muscarinic receptors in order to provide cells responsive to cholinergic agonists, such as Carbachol. The M1WT3 cells were grown in Ham's F12 medium with 50 µg/ml G-148 (Geneticin), 10% fetal bovine serum, 200 mM glutamine, 1.0 mg/L streptomycin and 1000 units/L penicillin (growing medium) under 5% $CO_2$ at 37° C.

To initiate growth, $5\times10^4$ M1WT3 cell/well (200 µL/well) were sterilely plated in selected individual wells of a flat bottom 96-well microplate. The selected wells were comprised of the inner 60 wells. At least 3 of the inner wells, however, were left without cells to be used as control wells. The entire microplate then was covered with a loosely-fitting plastic cover that allowed gas exchange to the wells and the microplate was incubated at 37° C. for approximately 24 hours to allow cells to attach to bottom of each selected well with cells.

Twelve hours prior to measuring extracellular acidification the growing media was aspirated off with a vacuum system and replaced with 200 µL of starving media (growing media with 1 mg/ml bovine serum albumin in place of the 10% fetal bovine serum) and the cells were again placed under 5% $CO_2$ at 37° C. The microplate was then incubated for 12 hours. Within 30–60 minutes prior to monitoring the rates of extracellular acidification, the starving medium was aspirated off, the wells were rinsed with approximately 200 µL simple indicator medium (Table 2 components) and then filled with 200 µL of simple indicator medium. All media was warmed to 37° C. before addition to the cells.

The light absorbance of the individual wells of the 96-well microplate was read in a THERMOmax™ microplate absorbance reader modified to record the ratio of optical density at two wavelengths (560 nm/420 nm), kinetically at 37° C. for 15 minutes with automix on. The automix feature is described in the Operator's Manual for the THERMOmax™ instrument (Catalog No. 0112-0014) of Molecular Devices Corporation, Menlo Park, Calif. The automix feature provides for uniform mixing of the contents of each well of the multiassay plate for about 5 seconds, followed by measurement of optical density at the first wavelength (in this case 560 nm) in about 5 seconds, followed by a change in interference filter in about 1 second, followed by measurement of optical density at the second wavelength (in this case 420 nm) in about 5 seconds. Thus, all optical density measurements are completed within 11 seconds following termination of the agitation step and the time elapsed for any one well between measuring the optical density at the first and second wavelengths was 6 seconds. This was the minimum time between reading optical density at the first and second wavelengths possible with the THERMOmax™ instrument. Preferably the readings at the first and second wavelengths are made simultaneously.

Additionally, the contents of the microplate wells were not agitated between reading optical density at the first and second wavelengths so that the light scattering effects of the cells tended to be the same for the optical density measurements made at the first and second wavelengths for any one well. (The THERMOmax™ instrument permitted the measurements to made without moving the microplate between reading optical density at the first and second wavelengths.) The ratio of the light-scattering effects at the first and second wavelengths, therefore, tended to cancel so that each ratio of optical densities had a minimum of noise due to light-scattering effects. The reading cycle, with agitation, measuring absorbance at the first wavelength of light, changing the filter, and reading the absorbance at the second wavelength of light, was repeated at the rate of 3 cycles per minute (i.e. every 20 seconds).

At the end of the 15 minutes the reading cycles were stopped, the microplate was removed and the media was quickly aspirated off and replaced with simple indicator media containing a cell-affecting agent, in this case 0 to 300 µM Carbachol. The reading cycles then were repeated, as above, for two consecutive 15 minute data collection periods followed by one final 30 minute data collection period. Approximately 2 minutes elapsed between stopping and restarting each of the data collection periods.

The ratio of optical density at the first and second wavelengths (i.e. 560 nm/420 nm in this case) for each well of the microplate, measured during each 20 second reading cycle was calculated by the microprocessor of the THERMOmax™ instrument. These data ratios then were transferred electronically by cable to a computer where the base 10 logarithm of these ratios ($\log_{10}$ R) then was calculated. The rate of change in $\log_{10}$ R gives the rate of change in pH directly if the effects of temperature, light-scattering, etc. are negligible. These apparent rates of pH change were measured by least-squares fitting of the experimental data for each well measured over each 15 or 30 minute interval. The apparent rates of pH change in selected wells without cells were subtracted from the apparent rates of pH change in the wells with cells. These data together with the relatively constant amount of pH buffer capacity of the medium and the constant number of cells placed in each well were used to calculate the extracellular acidification rate (expressed as the number of protons/cell/sec) for the cells in each well of the microplate for each 15 or 30 minute data collection interval. The results are shown in Table 4, which also show the incremental extracellular acidification rate of the cells (calculated as the number of protons/cell/sec) caused by the addition of 3, 10, 30, or 300 µM Carbachol to the medium of the cells prior to the measurement of extracellular acidification rate.

Often it is desirable to control for variation in the numbers of cells in each well of a multiassay plate. A convenient way to do this is to compare the rates of extracellular acidification in the same well before and after treatment with a cell-affecting agent. Shown in the sixth column of Table 4 is the % of change in mean extracellular acidification rate of triplicate wells subsequent to addition of the cell-affecting agent (in this case Carbachol). Specifically, as shown in the seventh column of Table 4, the % change in extracellular acidification rate of the cells with no cell-affecting agent may be subtracted to obtain the specific effect of the cell-affecting agent. The device and method of the present invention can be used to measure the % change in the extracellular acidification rate of the cells from one data collection period to the next.

Further, this device and method of the present invention can be used to measure the extracellular acidification rate of cells for many different cell-affecting agents. In some cases, for example, the present invention can be used for monitoring the toxicity effects of a cell-affecting agent—yielding information that may be of great interest to an investigator. The toxic effects of foods, drugs, cosmetic products, household detergents, and cleaning agents, for example could be measured using the present invention.

Also, the effect of known chemotherapeutic agents on existing tumor cell lines, or tumor cells obtained from cancer patients, could be tested with the present invention. With this information, the optimal concentrations or the optimal combinations of chemotherapeutic agents could be selected for treating each individual patient. Similarly, unknown chemotherapeutic agents or unknown drugs specific for individual receptors could be determined. Many examples of the effects of inhibitory and stimulatory cell-affecting agents on extracellular acidification rates of cells are disclosed in the following publications. Parce, J. W., Owicki, J. C., Kereso, K. M., Sigal, G. B., Wada, H. G., Muir, V. C., Bousse, L. J., Ross, K. L., Sikic, B. I. and McConnell, H. M: Detection of cell affecting agents with a silicon biosensor. *Science* 246: 243–247 (1989); Owicki, J. C. and Parce, J. W.: Bioassays with a microphysiometer. *Nature* 344: 271-272 (1990); Owicki, J. C., Parce, J. W., Kersco, K. M., Sigal, G. B., Muir, V. C., Venter, J. C., Fraser, C. M. and McConnell, H. M.: Continuous monitoring of receptor-mediated changes in the metabolic rates of living cells. *Proc. Natl. Acad. Sci. U.S.A.* 87: 4007–4011 (1990); Parce, J. W., Sigal, G. B., Kercso, K. M. and Owicki, J. C.: The silicon microphysiometer: detection of biological effects of chemical and biochemical agents by alterations of cellular metabolic rate. In *Biosensor Technology, Fundamentals and Applications* (Buck, R. P., Hatfield, W. E., Umana, M. and Bowden, E. R., eds.), Marcel Dekker, Inc., New York, N.Y. (1990) 367–373; Parce, J. W., Owicki, J. C. and Kercso, K. M.: Biosensors for directly measuring cell-affecting agents. *Annales de Biologie Clinique* 48: 639–641 (1990); Wada, H. G., Owicki, J. C. and Parce, J. W.: Cells on silicon: Bioassays with a microphysiometer. *Clinical Chemistry* 37: 600–601, (1991); Bruner, L.

H., Miller, K. R., Owicki, J. C., Parce, J. W. and Muir, V. C.: Testing ocular irritancy in vitro with the silicon microphysiometer. *Toxicology In Vitro* 5: 277–284 (1991); Parce, J. W., Owicki, J. C., Wada, H. G. and Kercso, K. M.: Cells on silicon: The Microphysiometer. In *Vitro Toxicology: Mechanisms and New Technology in Alternative Methods in Toxicology Series.* Volume 8, pp. 97–106 (Alan M. Goldberg, ed.) Mary Ann Liebert, Inc., New York, N.Y. (1991); McConnell, H. M., Rice, P., Wada, H. G., Owicki, J. C. and Parce, J. W.: The microphysiometer biosensor. *Current Opinion in Structural Biology* 1: 647–652 (1991); Raley-Susman, K. M., Miller, K. R., Owicki, J. C. and Sapolsky, R. M.: Effects of excitotoxin exposure on metabolic rate of primary hippocampal cultures: application of silicon microphysiometry to neurobiology. *J. Neuroscience* 12: 773–780 (1992); Owicki, J. C. and Parce, J. W.: Biosensors based on the energy metabolism of living cells: the physical chemistry and cell biology of extracellular acidification. *Biosensors and Bioelectronics* 7: 255–272 (1992); Nag, B., Wada, H. G., Fok, K. S., Green, D. J., Sharma, S. D., Clark, B. R., Parce, J. W. and McConnell, H. M.: Antigen-specific stimulation of T cell extracellular acidification by MHC class II-peptide complexes. *J. Immunol* 148: 2040–2044 (1992); McConnell, H. M., Owicki, J. C., Parce, J. W., Miller, D. L., Baxter, G. T., Wada, H. G. and Pitchford, S.: The Cytosensor microphysiometer: Biological applications of silicon technology. *Science* 257: 1906–1912 (1992); Wada, H. G., Indelicato, S. R., Meyer, L., Kitamura, T., Miyajima, A., Kirk, G., Muir, V. C. and Parce, J. W.: GM-CSF triggers a rapid glucose dependent extracellular acidification by TF-1 cells. Evidence for sodium/proton antiporter and PKC mediated activation of acid production. *J. Cell. Physiol.* 154: 129–138 (1993); Wada, H. G., Owicki, J. C., Bruner, L. H., Miller, K. R., Raley-Sussman, K. M., Panfili, P. R., Humphries, G. M. K. and Parce, J. W.: Measurement of cellular responses to toxic agents using a silicon microphysiometer. *Alternatives to Animal Testing and Experiments* 1: 154–164 (1992); Baxter, G. T., Miller, D. L., Kuo, R. C., Wada, H. G. and Owicki, J. C.: PKC is involved in GM-CSF signal transduction. Evidence from microphysiometry and antisense oligonucleotide experiments. *Biochemistry* 31: 10950–10954 (1992); Miller, D. L., Olson, J. C., Parce, J. W. and Owicki, J. C.: Cholinergic stimulation of the Na+/K+ ATPase as revealed by microphysiometry. *Biophys. J.* 64: 813–823 (1993); Nag, B., Wada, H. G., Passmore, D., Clark, B. R., Sharma, S. D. and McConnell, H. M.: Purified β-chain of MHC class II binds to CD4 molecules on transfected HeLa cells. *J. Immunol.* 150: 1358–1364 (1993); Nag, B., Wada, H. G., Deshpande, S. V., Passmore, D., Kendrick, T., Sharma, S. D., Clark, B. R. and McConnell, H. M.: Stimulation of T cells by antigenic peptide complexed with isolated chains of major histocompatibility complex class II molecules. *Proc. Natl. Acad. Sci. USA* 90: 1604–1608 (1993).

Higher time resolution in the rate of change in extracellular acidification rates may be obtained in a similar fashion by taking the derivative of the log R vs. time data. In the above cited case, data collection cycles are repeated at 20 second intervals. Thus, the time resolution of the system is 20 seconds. In some cases, more rapid time resolution may be desirable and in such cases the data collection cycle period can be shortened. The minimum data collection cycle is 17 seconds with the THERMOmax™ instrument, which employs 5 seconds agitation, 1 second settling time, 5 seconds for measurement of the optical density at the first wavelength, 1 second for changing the interference filter, and 5 seconds for measurement of the optical density at the second wavelength. Modification of the instrument to reduce the time for each of these measurement steps would provide for a system with time resolution shorter than 17 seconds.

An optimal instrument for the carrying out the above method would measure the optical density of the individual wells of the multiassay plate simultaneously rather than consecutively. Simultaneous measurements at two, or more, wavelengths would minimize the possibility of temporal changes in light scattering or absorbance in the individual wells. Also, the length of the reading cycle could be further reduced by simultaneous measurements of optical density at more than one wavelength. Thus, both precision and time resolution of monitoring pH changes in the individual wells would be improved.

An ideal instrument for this purpose could be constructed, for example, by simultaneously passing light comprising more than one wavelength through the individual wells of the multiassay plate and subsequently dispersing the light according to wavelength. This could be accomplished, for example, by means of a prism or grating, and providing two or more photodetectors to monitor light transmission simultaneously at two or more wavelengths. By way of example, the THERMOmax™ instrument could be used, as in the above example, to provide a chamber with uniform temperature, agitation, and light to the top of the individual wells of the multiassay plate. The THERMOmax™ instrument employs a light-collecting lens and a photodetector below each well of a 96-well multiassay plate. In the THERMOmax™ instrument the light passes through the individual wells of the multiassay plate and through the light-collecting lenses and onto the photodetectors. See for example, FIG. 6.

In the ideal instrument for this application, the 96 photodetectors would be replaced by an array of 96 optical fibers or light pipes to transmit the light to a spectrometer, comprising a grating or prism, where the light would be dispersed onto a diode-array detector for simultaneous monitoring of optical density at two or more selected wavelengths (560 nm and 420 nm in the instant example). For example, a 1024 element diode array would provide for 1024 simultaneous measurements at 1024 different wavelengths. The 96 optical fibers or light pipes could be brought as a bundle to the spectrometer and could be arranged linearly parallel to a light slit placed in front of the spectrometer, or alternatively, could first be reduced to a single optical fiber or light pipe before going to the spectrometer.

One method of reducing the light to single optical fiber or light pipe would be to employ a second rotor similar to the one presently employed in the THERMOmax™ instrument and described in U.S. Pat. Nos. 4,968,148 and 5,112,134. The second rotor in this case would employ a reversed light path where the light passes from one of the 96 fibers into the rotor and then into the single fiber, where it is subsequently transmitted to the spectrometer.

By way of example, a suitable spectrometer for the present method can be Ocean Optics Catalog # SD 1000 Dual Fiber Optic Spectrometer. A suitable grating for monitoring the selected wavelengths would be Ocean Optics Grating #3 for dispersing light in the 360 nm to 850 nm range. Ocean Optics Data Acquisition Board CIODAS-AT with accompanying software could be employed in a suitable personal computer to analyze the data and to provide for calculation of the rates of pH change in the individual wells of a multiassay plate. A suitable optical fiber for carrying the light from the multiassay plate to the spectrometer, for example, can be Ocean Optics Catalog # 16-200S-2-SMA- GR. Suitable collimating lenses for directing the light from the wells of the multiassay plate into the optical fiber are Ocean Optics Catalog # 74-04-SMA-GR0.250, which are in a 0.25 inch housing. One lens is employed to direct the light into each of the 96 optical fibers. The optical resolution in this configuration is 10 nm, the same as was used in the above example employing the THERMOmax™ instrument. The above components may be obtained from Ocean Optics, Inc., Dunedin, Fla. The second spectrometer of the SD 1000 Dual Fiber Optic Spectrometer may be used to monitor fluctuations in light intensity, at each individual wavelength, due to fluctuations in the light source as described by the product literature provided by Ocean Optics and is generally known to those skilled in the art of double-beam spectrometer design.

EXAMPLE 9

The cell effects of beta-Maleimido proprionic acid (NMPA), N-Ethyl maleimide (NEM), Ferricyanide $(Fe_3CN)^{-3}$ (i.e. FeCN) and Cupric o-phenanthroline (Cu o-Ph) on the activation of TF-1 cells by GM-CSF was measured by a procedure similar to that used in Example 5. TF-1 cells were starved overnight in media lacking GM-CSF. The cells were washed twice and re-suspended in simple indicator medium at $1 \times 10^6$ cells/ml. The simple indicator medium contained one of the following test substances: NMPA, MEM, FeCN or Cu o-Ph at the tested concentration. A control test, which had no cell-affecting agent, was run in parallel. The cells in the simple indicator medium with or without cell-affecting agents were warmed to 37° C. for 20 minutes prior to the addition of recombinant human GM-CSF (obtained from Sandoz/Schering-Plough Corp.) to a final concentration of 0.1 ng/ml, and the extracellular acidification rate was measured by monitoring OD560/OD420 at 37° C. for 45 minutes. Additionally, a set of cells were mock treated with an equal volume of simple indicator medium but without any GM-CSF as a control for GM-CSF activation. The acidification rates were calculated from the slope of log(OD560/OD420) from 20 to 40 minutes after addition of the GM-CSF.

Generally, 0.1 ng/ml of GM-CSF caused a 100–150% increase in extracellular acidification rate. The cell-affecting agents inhibited the response of extracellular acidification to GM-CSF. Thus, these cell-affecting agents are inhibitory cell-affecting agents, while GM-CSF is a stimulatory cell-affecting agent. The measurements were made in duplicate and results are shown below as % inhibition of the response to GM-CSF, relative to control cells which received GM-CSF only.

| Cell Affecting Agent | Concentration | % Inhibition GM-CSF Response |
|---|---|---|
| NMPA | 10 µM | 3 |
| NEM | 10 µM | 98 |
| FeCN | 100 µM | 5 |
| Cu o-Ph | 25 µM | 43 |

The results show that 10 µM NEM inhibited the GM-CSF activation by 98% and 25 µM Cu o-Ph inhibited the GM-CSF activation by 43%. The inhibitory effects of NMPA and FeCN were weak in comparison to NEM and Cu o-Ph.

TABLE 1

Formulation of a Complete Medium

| | mg/L |
|---|---|
| Sodium Chloride | 6660. |
| Potassium Chloride | 400. |
| Glucose (Dextrose) (anhyd.) | 20000. |
| L-Arginine.HCl | 241.88 |
| L-Asparagine.H$_2$O | 56.82 |
| L-Aspartic Acid | 20.0 |
| L-Cystine.2HCl.H$_2$O | 65.18 |
| L-Glutamic Acid | 20.0 |
| L-Glutamine | 300. |
| Glycine | 10.0 |
| L-Histidine.HCl.H$_2$O | 20.27 |
| Hydroxyproline | 20.0 |
| L-Isoleucine | 50.0 |
| L-Leucine | 50.0 |
| L-Lysine.HCl | 40.0 |
| L-Methionine | 15.0 |
| L-Phenylalanine | 15.0 |
| L-Proline | 20.0 |
| L-Serine | 30.0 |
| L-Threonine | 20.0 |
| L-Tryptophan | 5.00 |
| L-Tyrosine.2Na.2H$_2$O | 28.83 |
| L-Valine | 20.0 |
| Inositol | 35.0 |
| Phenol Red, Na salt | 205. |
| Calcium Nitrate, Ca(NO$_3$)$_2$.4H$_2$O | 100. |
| Choline Chloride | 3.00 |
| Magnesium Sulfate, anhyd., MgSO$_4$ | 48.84 |
| p-Aminobenzoic Acid | 1.00 |
| Folic Acid | 1.00 |
| Nicotinic Acid Amide | 1.00 |
| Pyridoxine.HCl | 1.00 |
| Riboflavin | 0.20 |
| Thiamine.HCl | 1.00 |
| d-Biotin | 0.20 |
| Glutathione, reduced | 1.00 |
| Pantothenic Acid, Ca salt | 0.25 |
| Vitamin B$_{12}$ | 0.005 |
| Sodium Phospate | |
| NaH$_2$PO$_4$.2H$_2$O | 40.6 |
| Na$_2$HPO$_4$(anhyd.) | 141. |
| Human Serum Albumin | 1000. |
| Streptomycin | 1.00 |

TABLE 2

Formulation of a Simple Medium

| | mM |
|---|---|
| MgCl$_2$.6H$_2$O | 0.60 |
| KCl | 3.00 |
| KH$_2$PO$_4$(anhyd.) | 1.00 |
| D-Glucose | 10.0 |
| CaCl$_2$.2H$_2$O | 0.30 |
| NaCl | 130. |
| HEPES | 0.70 |
| Phenol Red | 0.27 |
| Human Serum Albumin | 1.0 mg/ml |

TABLE 3

KODAK pH indicators

| Chem No. | Indicator | pH Range and Color Change | | | |
|---|---|---|---|---|---|
| 1309 | Methyl Violet | Y | 0.0 | — | 1.6B |
| 1350 | Crystal Violet | Y | 0.0 | — | 1.8B |
| 1765 | Ethyl Violet | Y | 0.0 | — | 3.5B |
| 624 | Brilliant Green | Y | 0.0 | — | 2.6G |
| 1264 | Malachite Green Oxalate | Y | 0.2 | — | 1.8B |
| 1767 | Methyl Green | Y | 0.2 | — | 1.8B |
| 744 | *Cresol Red | R | 1.0 | — | 2.0Y |
| 1361 | Quinaldine Red | C | 1.0 | — | 2.2R |
| 926 | p-(p-Dimethylaminophenylazo)benzoic Acid Sodium Salt (Para Methyl Red) | R | 1.0 | — | 3.0Y |
| 766 | Metanil Yellow | R | 1.2 | — | 2.4Y |
| 1714 | 4-Phenylazodiphenylamine | R | 1.2 | — | 2.5Y |
| 753 | *Thymol Blue | R | 1.2 | — | 2.8Y |
| 2118 | *m-Cresol Purple | R | 1.2 | — | 2.8Y |
| 823 | Orange IV | R | 1.4 | — | 2.8Y |
| 110 | Erythrosin B | O | 2.2 | — | 3.6R |
| 1021 | Benzopurpurin 4B | V | 2.2 | — | 4.2R |
| 2718 | Stains-all | C | 2.4 | — | 3.4P |
| 7083 | Tetrabromophenolphthelein Ethyl Ester Potassium Salt | Y | 3.0 | — | 4.2B |
| 752 | *Bromophenyl Blue | Y | 3.0 | — | 4.26 |
| 770 | Congo Red | B | 3.0 | — | 5.0R |
| 8756 | 3-Nitrosalicylaldehyde | C | 3.0 | — | 5.0Y |
| 2216 | Methyl Orange-Xylene Cyanol Solution | P | 3.2 | — | 4.2G |
| 14330 | Methyl Orange | R | 3.2 | — | 4.4Y |
| 122 | Ethyl Orange | R | 3.5 | — | 4.8Y |
| 1954 | 3-(4-Dimthylamino-1-naphthylazo)-4-methoxybenzenesulfonic Acid | V | 3.5 | — | 4.8Y |
| 1782 | *Bromocresol Green | Y | 3.8 | — | 5.4B |
| 2108 | Resazurin | O | 3.8 | — | 6.4V |
| 2155 | Ethyl Red | C | 4.0 | — | 5.8R |
| 4953 | Universal Indicator Solution | R | 4.0 | — | 8.5BG |
| 431 | Methyl Red | K | 4.2 | — | 6.2Y |
| 1051 | Alizarin Red S | Y | 4.6 | — | 6.0R |
| 944 | Propyl Red | R | 4.6 | — | 6.6Y |
| 191 | o-Nitrophenol | C | 5.0 | — | 6.2Y |
| 6361 | Mordent Black 11 | R | 5.0 | — | 6.5B |
| 745 | *Bromocresol Purple | Y | 5.2 | — | 6.8P |
| 2116 | Chlorophenol Red | Y | 5.2 | — | 8.0R |
| 192 | *p-Nitrophenol | C | 5.4 | — | 6.6Y |
| 1014 | Alizarin | Y | 5.6 | — | 7.2R |
| 7121 | Nitrazine Yellow | Y | 6.0 | — | 7.0B |
| 839 | *Bromothymol Blue | Y | 6.0 | — | 7.6B |
| 837 | Brilliant Yellow | Y | 6.6 | — | 8.0O |
| 541 | *Phenol Red | Y | 6.8 | — | 8.2R |
| 725 | Neutral Red | R | 6.8 | — | 8.0A |
| 1340 | m-Nitrophenol | C | 6.6 | — | 8.6Y |
| 744 | *Cresol Red | Y | 7.0 | — | 8.6R |
| 1179 | Curcumin | Y | 7.4 | — | 8.6R |
| 2118 | *m-Cresol Purple | Y | 7.4 | — | 9.0P |
| 7069 | 4,4'-Bis(4-amino-1-naphthylazo-2,2'-atilbenedisulfonic Acid | B | 8.0 | — | 9.0R |
| 753 | *Thymol Blue | Y | 8.0 | — | 9.3E |
| 202 | *Phenolphthalsin | C | 8.0 | — | 10.0R |
| 774 | o-Cresolphthaisin | C | 8.2 | — | 9.8R |
| 924 | p-Naphtholbenzein | C | 8.2 | — | 10.0B |
| 5488 | Ethyl Biz(2,4-dinitrophenyl) Acetate | C | 8.4 | — | 9.6B |
| 1091 | Thymolphthalein | C | 8.8 | — | 10.5B |
| 8679 | Nile Blue A | B | 9.4 | — | 10.6R |
| 764 | Alizarin Yellow R | Y | 10.0 | — | 12.0R |
| 1170 | Curcumin | R | 10.2 | — | 11.8O |
| 1014 | Alizarin | R | 8.2 | — | 12.4P |
| 1008 | Indigo Carmine | B | 11.4 | — | 13.8Y |

A-amber
B-blue
C-colorless
G-green
K-pink
O-orange
P-purple
R-red
V-violet
Y-yellow

TABLE 3-continued

*These indicators are also available as the sodium salt, directly soluble in water.

Redox Indicators

| Chem No. | Chemical | Potential at pH0a (Volts) | Color* Reduced | Oxidized |
|---|---|---|---|---|
| 725 | Neutral Red | −0.24 | C | R |
| 9768 | N,N-Dimethylindoaniline | 0.22 | C | B |
| 9678 | Nile Blue A | 0.29 | C | B |
| 573 | Methylene Blue | 0.53 | C | B |
| 1755 | Thionin | 0.56 | C | V |
| 1743 | Brilliant Cresyl Blue | 0.58 | C | B |
| 3463 | 2,6-Dichloroindophenol Sodium Salt | 0.67 | C | R |
| 7700 | N-(p-Methoxyphenyl)-p-phenylanediamine Hydrochloride | 0.71 | C | B |
| 509 | 3,3'-Dimethoxybenzidine | 0.76 | C | R |
| 6748 | 3,3'-Dimethoxybenzidine Dihydrochloride | 0.76 |   | R |
| 2147 | N,N-Dimethyl-p-phenylanediamine | 0.76 | C | R |
| 1797 | N,N-Diphenylbenzidine | 0.76 | C | V |
| 105 | Diphenylamine | 0.76 | C | V |
| 5314 | p-Ethoxyphenylazo-m-phenylanediamine Monohydrochloride | 0.76 | R | V |
| 5897 | Diphenylaminosulfonic Acid Sodium Salt | 0.85 | C | V |
| 3104 | Barium Diphenylaminesulfonate | 0.85 | C | V |
| 249 | o-Tolidine | 0.87 | C | B |
| 56935 | Xylene Cyanol FF | 1.00 | — | — |
| 2222 | N-Phenylanthranilic Acid | 1.08 | C | P |
| 8941 | Tris(1,10-phenanthroline)Iron(R) Sulfate | 1.14 | R | B |
| 10001 | Dicyanobis(1,10-phenanthroline)Iron | 1.41 | R | B |
| 1021 | Benzopurpurin 4B | — | B | C |
| 9763 | Naphthol Blue Black | — | B | C |

*B-blue
C-colorless
P-pink
R-red
V-violet
Y-yellow

TABLE 4

Carbachol Stimulation of M1WT3 cells in a THERMOmax™ microplate reader

| Treatment | ΔpH/Sec* | CV | Protons/ Cell · Sec | ΔProtons/Cell · Sec minus 0 Carboachol | % Change compared to pre-Carbachol | % Change compared to pre-Carbachol minus 0 Carbachol |
|---|---|---|---|---|---|---|
| 0 μM pre-Cabachol (15 min) | 6.5909E − 05 | 3.38% | 6.60E + 07 | — | — | — |
| 3 μM pre-Cabachol (15 min) | 6.7523E − 05 | 3.44% | 6.76E + 07 | — | — | — |
| 10 μM pre-Cabachol (15 min) | 6.3289E − 05 | 8.20% | 6.34E + 07 | — | — | — |
| 30 μM pre-Cabachol (15 min) | 6.1289E − 05 | 3.28% | 6.14E + 07 | — | — | — |
| 300 μM pre-Cabachol (15 min) | 5.7183E − 05 | 6.75% | 5.72E + 07 | — | — | — |
| 0 μM Cabachol (First 15 min) | 6.1536E − 05 | 3.32% | 6.16E + 07 | 0 | −6.63% | 0 |
| 3 μM Cabachol (First 15 min) | 7.1534E − 05 | 4.55% | 7.16E − 07 | 1.00E + 07 | 5.94% | 12.58% |
| 10 μM Cabachol (First 15 min) | 7.5928E − 05 | 2.14% | 7.60E − 07 | 1.44E + 07 | 19.97% | 26.61% |
| 30 μM Cabachol (First 15 min) | 7.2713E − 05 | 3.83% | 7.28E − 07 | 1.12E + 07 | 18.64% | 25.27% |
| 300 μM Cabachol (First 15 min) | 8.8294E − 05 | 11.88% | 6.84E − 07 | 6.76E + 06 | 19.43% | 26.07% |
| 0 μM Cabachol (Second 15 min) | 4.1378E − 05 | 2.03% | 4.14E − 07 | 0 | −37.22% | 0 |
| 3 μM Cabachol (Second 15 min) | 5.2542E − 05 | 2.20% | 5.26E − 07 | 1.12E − 07 | −22.19% | 15.03% |
| 10 μM Cabachol (Second 15 min) | 5.6378E − 05 | 1.76% | 5.64E − 07 | 1.50E − 07 | −10.92% | 26.30% |
| 30 μM Cabachol (Second 15 min) | 5.6101E − 05 | 4.56% | 5.62E − 07 | 1.47E − 07 | −8.46% | 28.75% |
| 300 μM Cabachol (Second 15 min) | 5.2420E − 05 | 6.61% | 5.25E − 07 | 1.11E − 07 | −8.33% | 28.89% |
| 0 μM Cabachol (Last 30 min) | 3.6091E − 05 | 4.32% | 3.61E − 07 | 0 | −45.24% | 0 |
| 3 μM Cabachol (Last 30 min) | 5.0490E − 05 | 1.79% | 5.05E − 07 | 1.44E − 07 | −25.23% | 20.02% |
| 10 μM Cabachol (Last 30 min) | 5.7103E − 05 | 3.12% | 5.72E − 07 | 2.10E − 07 | −9.77% | 35.47% |
| 30 μM Cabachol (Last 30 min) | 5.7641E − 05 | 4.04% | 5.79E − 07 | 2.18E − 07 | −5.63% | 39.62% |
| 300 μM Cabachol (Last 30 min) | 5.2560E − 05 | 8.45% | 5.26E − 07 | 1.65E − 07 | −8.08% | 37.16% |

*Mean of triplicate determinations

What is claimed is:

1. A method for measuring the effects of cell metabolism affecting agents on cells retained in individual wells of a multiassay plate by measuring the rates of extracellular acidification, comprising the steps of:

(a) placing the cells in a solution containing pH buffer and an acid/base indicator, the acidic form having an optimum absorbance in a first wavelength region and the basic form having an optimum absorbance in a second wavelength region, (b) adding a cell metabolism affecting agent to one or more, of the individual wells of the multiassay plate, (c) heating the solution in each of the individual wells of the multiassay plate to substantially uniform temperature, (d) mixing, simultaneously, the solution in each well of the multiassay plate for a first predetermined time, (e) measuring optical density of light passing vertically through the wells of the multiassay plate both at the first wavelength in the first wavelength region and at a second wavelength in the second wavelength region, (f) determining the ratio of the optical density at the first and second wavelengths in each of two, or more, wells of the multiassay plate, (g) repeating steps (c), (d), (e), and (t) so as to effect repetitive measurements of the ratio of optical densities at predetermined time intervals within about an hour, wherein the repeating is done in relatively rapid succession within 13 seconds, (h) analyzing the repetitive measurements and indicating the rate of change within a selected time interval within about the one hour so as to monitor kinetically the rate of change in extracellular pH caused by the cells within the selected time interval, and (i) comparing the rate of change in extracellular pH caused by the cells in wells containing the metabolism affecting agent to the wells with a lower concentration of the metabolism affecting agent.

2. The method of claim 1, wherein the measuring step additionally comprises measuring optical density of light passing vertically through the wells of the multiassay plate at a third wavelength in a third wavelength region, wherein absorbance of the acid/base indicator does not change substantially in the third wavelength region when pH or temperature is varied, and wherein the determining step comprises calculating the ratio R wherein R is the quantity: (the optical density at the first wavelength minus the optical density at the third wavelength) divided by (the optical density at the second wavelength minus the optical density at the third wavelength).

3. The method of claim 1, wherein the determining step additionally comprises calculating the logarithm of R.

4. The method of claim 2, wherein the determining step additionally comprises calculating the logarithm of R.

5. The method of claim 1 wherein the measuring step additionally comprises measuring the optical density at the first and the second wavelengths.

6. The method of claim 5 wherein the measuring additionally comprises measuring the optical density at the first and the second wavelengths in the same reading cycle.

7. The method of claim 5 wherein the measuring additionally comprises measuring the optical density at the first and the second wavelengths simultaneously.

8. The method of claim 5 wherein the measuring additionally comprises measuring the optical density at the first and the second wavelengths in succession of about 10 seconds, or 13 seconds when 3 seconds of agitation is utilized between subsequent reads of a single sample well.

9. The method of claim 2 wherein the measuring step additionally comprises measuring the optical density at the first, second, and third wavelengths.

10. The method of claim 9 wherein the measuring additionally comprises measuring the optical density at the first, second and third wavelengths in the same reading cycle.

11. The method of claim 9 wherein the measuring additionally comprises measuring the optical density at the first, second and third wavelengths simultaneously.

12. The method of claim 9 wherein the measuring step additionally comprises measuring the optical density at the first, second and third wavelengths in succession of about 10 seconds, or 13 seconds when 3 seconds of agitation is utilized between subsequent reads of a single sample well.

13. The method of claim 1, wherein the buffer maintains substantially the same ratio of the acidic and basic forms of the acid/base indicator with changes in temperature.

14. The method of claim 2, wherein the buffer maintains substantially the same ratio of the acidic and basic forms of the acid/base indicator with changes in temperature.

15. The method of claim 13, wherein the acid/base indicator is phenol red and the buffer comprises a phosphate buffer.

16. The method of claim 15, wherein the buffer also comprises an amine buffer.

17. The method of claim 16, wherein the amine buffer comprises a HEPES buffer.

18. The method of claim 17, wherein additionally, a cell metabolism-affecting agent is added to one or more, of the wells of the multiassay plate and the rate of change in the extracellular pH caused by the cells in wells with the metabolism-affecting agent is compared to the rate of change in extracellular pH caused by the cells in wells containing a lower concentration of cell metabolism-affecting agent.

19. The method of claim 13, wherein additionally, a cell metabolism-affecting agent is added to one or more, of the wells of the multiassay plate and the rate of change in the extracellular pH caused by the cells in wells with the metabolism-affecting agent is compared to the rate of change in extracellular pH caused by the cells in wells containing a lower concentration of cell metabolism-affecting agent.

20. A microplate reader device comprising:

(a) a means for passing light vertically through contents of wells of a multiassay plate, (b) means for heating the contents to substantially the same temperature, (c) means for simultaneously agitating the contents, (d) means for measuring optical density at two, or more wavelengths of light passing vertically through the contents of each well of the multiassay plate, (e) means for calculating a ratio of optical densities at two or more wavelengths of light passing vertically through the contents, (f) means for effecting repetitive measurements of the ratio of optical densities in relatively rapid succession within 13 seconds, and (g) means for calculating either a rate of change in the ratio of optical densities or a rate of change in a logarithm of the ratio of optical densities.

21. The device of claim 20 wherein the ratio of optical densities comprises R wherein R is the quantity: (the optical density at the first wavelength minus the optical density at the third wavelength) divided by (the optical density at the second wavelength minus the optical density at the third wavelength).

22. The device of claim 20 wherein, the means for calculating either a rate change in the ratio of optical densities or a rate of change in a logarithm of the ratio of the optical densities comprises a means for calculating a rate in change in a logarithm of the ratio of optical densities.

23. The device of claim 21 wherein, the means for calculating either a rate change in the ratio of optical densities or a rate of change in a logarithm of the ratio of the optical densities comprises a means for calculating a rate in change in a logarithm of the ratio of optical densities.

24. The device of claim 20 wherein the means for measuring optical density at the two, or three wavelengths comprises means for measuring optical densities at a first wavelength and at a second wavelength, simultaneously.

25. The device of claim 21 wherein the means for measuring optical density at the two, or three wavelengths comprises means for measuring optical densities at a first wavelength and at a second wavelength, simultaneously.

26. The device of claim 23 wherein the means for measuring optical density at the two, or three wavelengths comprises means for measuring optical densities at a first wavelength and at a second wavelength, simultaneously.

27. A method for monitoring the metabolism in cells retained in individual wells of a multiassay plate by measuring the rates of extracellular acidification, comprising the steps of:

(a) placing the cells in a solution containing a pH buffer and an acid/base indicator, the acidic form having optimum absorbance in a first wavelength region and the basic form having optimum absorbance in a second wavelength region, (b) heating the solution in each of the individual wells of the multiassay plate to a substantially uniform temperature, (c) mixing, simultaneously, the solution in each well of the multiassay plate for a first predetermined time, (d) repeating step (c) to monitor kinetically the rate of change in extracellular pH caused by the cells.

28. A device for carrying out a method or placing cells in a solution containing a pH buffer and an acid/base indicator, the acidic form having optimum absorbance in a first wavelength region and the basic form having optimum absorbance in a second wavelengths region, heating the solution in each of the individual wells of a multiassay plate to a substantially uniform temperature, mixing, simultaneously, the solution in each well of the multiassay plate for a predetermined time, measuring optical density of light passing vertically through the wells of the multiassay plate both at a first wavelengths in the first wavelength region and at a second wavelength in the second wavelength region, determining a ratio of the optical density at the first and second wavelengths in each of two or more wells of the multiassay plate, and repeating the steps of mixing, measuring the optical densities and determining the ratio of optical densities to monitor kinetically the rate of change in extracellular pH caused by the cells, the device comprising:

(a) a microplate reader which passes light vertically through the wells of the microplate and means for measuring optical density at two, or more, wavelengths of light passing vertically through solutions in the wells of the microplate;

(b) means for simultaneously agitating the solutions;

(c) means for heating the solutions to substantially the same temperature; and (d) means for calculating either a rate of change on the ratio of optical densities or a rate of change in a logarithm of the ratio of optical densities.

29. A method for monitoring the metabolism in cells retained in individual wells of a multiassay plate by measuring the rates of extracellular acidification, comprising the steps of (a) placing the cells in a solution containing a pH buffer and an acid/base indicator, the acidic form having optimum absorbance in a first wavelength region and the basic form having optimum absorbance in a second wavelength region, (b) heating the solution in each of the individual wells of the multiassay plate to a substantially uniform temperature, (c) mixing, simultaneously, the solution in each well of the multiassay plate for a first predetermined time, (d) measuring the optical density, and (e) repeating step (c) and (d) to monitor kinetically the rate of change in extracellular pH caused by the cells.

30. A microplate reader device comprising:

(a) a means for passing light vertically through contents of wells of a multiassay plate, (b) means for heating the contents to substantially the same temperature, (c) means for simultaneously agitating the contents, (d) means for measuring optical density at two, or more, wavelengths of light passing vertically through the contents of each well of the multiassay plate (e) means for calculating a ratio of optical densities at two or more wavelengths of light passing vertically through the contents, (f) means for effecting repetitive measurements of the ratio of optical densities at predetermined time intervals, wherein the repetitive measurements are done in relatively rapid succession within 13 seconds, and (g) means for calculating either a rate of change in the ratio of optical densities or a rate of change in a logarithm of the ratio of optical densities.

31. A microplate reader device according to claim 50, wherein the elapsed time between the agitating and the measuring steps is lees than about 11 seconds.

32. A microplate reader device comprising:

(a) a means for passing light vertically through contents of wells of a multiassay plate;

(b) means for heating the contents to substantially the same temperature;

(c) means for simultaneously agitating the contents;

(d) means for measuring optical density in the same reading cycle at three or more wavelengths of light passing vertically through the contents of each well of the multiassay plate;

(e) means for calculating a ratio of optical densities at three or more wavelengths of light passing vertically through the contents, wherein the ratio of optical densities comprises R wherein R is the quantity: (the optical density at a first wavelength minus the optical density at a third wavelength) divided by (the optical density at a second wavelength minus the optical density at the third wavelength);

(f) means for effecting repetitive measurements of the ratio of optical densities in relatively rapid succession within 13 seconds, and (g) means for calculating either a rate of change in the ratio of optical densities or a rate of change in a logarithm of the ratio of optical densities.

33. A microplate reader device comprising:

(a) a means for passing light vertically through contents of wells of a multiassay plate;

(b) means for heating the contents to substantially the same temperature;

(c) means for simultaneously agitating the contents, (d) means for measuring optical density at simultaneously at three or more wavelengths of light passing vertically through the contents of each well of the multiassay plate;

(e) means for calculating a ratio or optical densities at three or more wavelengths of light passing vertically through the contents,
   wherein the ratio of optical densities comprises R wherein R is the quantity: (the optical density at a first wavelength minute the optical density at a third wavelength) divided by (the optical density at a second wavelength minus the optical density at the third wavelength);

(f) means for effecting repetitive measurements of the ratio of optical densities in relatively rapid succession within 13 seconds; and (g) means for calculating either a rate of change in the ratio of optical densities or a rate of change in a logarithm of the ratio of optical densities.

34. A microplate reader device comprising:

(a) a means for passing light vertically through contents of wells of a multiassay plate;

(b) means for heating the contents to substantially the same temperature;

(c) means for simultaneously agitating the contents;

(d) means for measuring optical density at three or more wavelengths of light passing vertically through the contents of each well of the multiassay plate;

(e) the means for measuring further comprising means for measuring the optical density at first and second wavelengths, in succession of about ten seconds, or 13 seconds when 3 seconds of agitation is utilized between subsequent reads of a single sample well;

(f) means for calculating a ratio of optical densities at three or more wavelengths of light passing vertically through the contents, wherein the ratio of optical densities comprises R wherein R is the quantity: (the optical density at the first wavelength minus the optical density at a third wavelength) divided by (the optical density at the second wavelength minus the optical density at the third wavelength);

(g) means for effecting repetitive measurements of the ratio of optical densities in relatively rapid succession within 13 seconds; and (h) means for calculating either a rate of change in the ratio of optical densities or a rate of change in a logarithm of the ratio of optical densities.

35. A microplate reader device comprising:

(a) a means for passing light vertically through contents of wells of a multiassay plate;

(b) means for heating the contents to substantially the same temperature;

(c) means for simultaneously agitating the contents;

(d) means for measuring optical density in the same reading cycle at three or more wavelengths of light passing vertically through the contents o each well or the multiassay plate;

(e) means for calculating a ratio of optical densities at three or more wavelengths of light passing vertically through the contents;

(f) means for effecting repetitive measurements of the ratio of optical densities in relatively rapid succession within 13 seconds; and (g) means for calculating either a rate of change in the ratio of optical densities or a rate of change in a logarithm of the ratio of optical densities, which means comprise a means for calculating a rate in change in a logarithm of the ratio of optical densities.

36. A microplate reader device comprising:

(a) a means for passing light vertically through contents of wells of a multiassay plate;

(b) means for heating the contents to substantially the same temperature;

(c) means for simultaneously agitating the contents;

(d) means for measuring optical density simultaneously at three or more wavelengths of light passing vertically through the contents of each well of the multiassay plate;

(e) means for calculating a ratio of optical densities at three or more wavelengths of light passing vertically through the contents;

(f) means for effecting repetitive measurements of the ratio of optical densities in relatively rapid succession within 13 seconds; and (g) means for calculating either a rate of change in the ratio of optical densities or a rate of change in a logarithm of the ratio of optical densities, which means comprise a means for calculating a rate in change in a logarithm of the ratio of optical densities.

37. A microplate reader device comprising:

(a) a means for passing light vertically through contents of wells of a multiassay plate;

(b) means for heating the contents to substantially the same temperature;

(c) means for simultaneously agitating the contents;

(d) means for measuring optical density at three or more wavelengths of light passing vertically through the contents of each well of the multiassay plate;

(e) the means measuring additionally comprising means for measuring the optical density at first, second and third wavelengths in succession of about 10 seconds, or 13 seconds when three seconds of agitation is utilized, between subsequent reads of a single sample well;

(e) means for calculating a ratio of optical densities at three or more wavelengths of light passing vertically through the contents;

(f) means for effecting repetitive measurements of the ratio of optical densities in relatively rapid succession within 13 seconds; and (g) means for calculating either a rate of change in the ratio of optical densities or a rate of change in a logarithm of the ratio of optical densities, which means comprise a means for calculating a rate in change in a logarithm of the ratio of optical densities.

* * * * *